(12) United States Patent
Nagano et al.

(10) Patent No.: US 9,250,232 B2
(45) Date of Patent: Feb. 2, 2016

(54) FLUORESCENT PROBE

(71) Applicant: THE UNIVERSITY OF TOKYO, Tokyo (JP)

(72) Inventors: Tetsuo Nagano, Tokyo (JP); Kenjiro Hanaoka, Tokyo (JP); Kazuhisa Hirabayashi, Tokyo (JP); Yuko Toki, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 14/378,022

(22) PCT Filed: Feb. 15, 2013

(86) PCT No.: PCT/JP2013/053662
§ 371 (c)(1),
(2) Date: Mar. 27, 2015

(87) PCT Pub. No.: WO2013/122189
PCT Pub. Date: Aug. 22, 2013

(65) Prior Publication Data
US 2015/0212073 A1  Jul. 30, 2015

(30) Foreign Application Priority Data

Feb. 17, 2012  (JP) .................................. 2012-032373

(51) Int. Cl.
*C07H 17/04* (2006.01)
*G01N 33/52* (2006.01)
*C07F 7/08* (2006.01)

(52) U.S. Cl.
CPC .............. *G01N 33/52* (2013.01); *C07F 7/0816* (2013.01); *C07H 17/04* (2013.01)

(58) Field of Classification Search
CPC .................................. G01N 33/52; C07H 17/04
See application file for complete search history.

(56) References Cited

FOREIGN PATENT DOCUMENTS

| WO | 2010126077 A1 | 11/2010 |
| WO | 2012/083064 A1 | 6/2012 |
| WO | 2012/099218 A1 | 7/2012 |

OTHER PUBLICATIONS

Yang et al., Caplus an 2015:1286186, 2015.*
International Preliminary report on patentability for Application No. PCT/JP2013/053662, mail date is Aug. 19, 2014.
Q. Best, "Functionalization of a long wavelength silicon-analog rhodamine for fluorescence based imaging of biomolecules", Pacifichem 2010.
Takahiro Egawa et al., "Development of a fluorescein analogue, TokyoMagenta, as a novel scaffold for fluorescence probes in red region", Chem. commun., 2011, vol. 47, pp. 4162-4164.
Yuichiro Koide, "Evolution of Novel Rhodamines as platform for far-red to NIR emitting fluorescent probes", JSMI Report, pp. 8-9, May 14, 2009.
Search report from PCT/JP2013/053662, mail date is Apr. 16, 2013.

* cited by examiner

*Primary Examiner* — Sun Jae Yoo
(74) *Attorney, Agent, or Firm* — Greenblum & Bernstein, P.L.C.

(57) ABSTRACT

A compound represented by the formula (I) [$R^1$ represents hydrogen atom or a substituent; $R^2$, $R^3$, $R^6$, and $R^7$ represent hydrogen atom, an alkyl group, a halogen atom, or a hydrophilic substituent; $R^4$ and $R^5$ represent an alkyl group or an aryl group; $R^8$ and $R^9$ represent a group cleaved by contact with an object substance for measurement; and X represents silicon atom, germanium atom, or tin atom] or a salt thereof, which is useful as a fluorescent probe that emits red fluorescence by contact with an object substance for measurement.

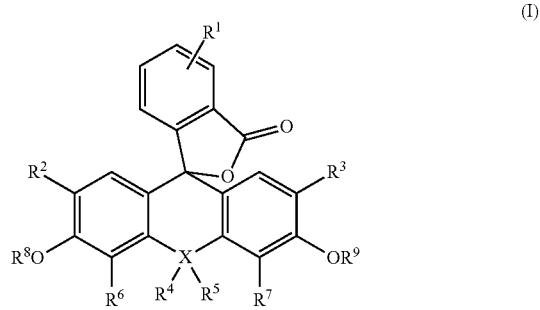

(I)

5 Claims, 6 Drawing Sheets
(2 of 6 Drawing Sheet(s) Filed in Color)

FLUORESCENT PROBE

TECHNICAL FIELD

The present invention relates to a novel fluorescent probe having a red fluorophore.

BACKGROUND ART

Fluorescein is a molecule reported in 1871, and has been widely used as a pH indicator or a labeling dye because of the high water solubility and high fluorescence quantum yield thereof. Since a calcium probe containing fluorescein as a mother nucleus was developed, there have been provided a large number of highly sensitive fluorescent off/on type probes utilizing intramolecular photoinduced electron transfer (PET), decyclization or cyclization of spiro ring, and the like. However, plural dyes containing fluorescein as a parent compound cannot be simultaneously used in molecular imaging, since fluorescence wavelengths thereof overlap with each other. Moreover, the probes utilizing the intramolecular photoinduced electron transfer suffer from a problem that such probes require precise design of the oxidation potential of the benzene ring, and therefore modification of the chemical structure is strictly limited.

A compound corresponding to the basic structure of rhodamine, pyronin Y (PY), of which oxygen atom is replaced with silicon atom (TMDHS) and application of this compound as a fluorescent probe have already been reported (Best, Q et al., Pacifichem 2010, subject number 2335, Dec. 19, 2010; Yuichiro KOIDE et al., Fourth Convention of The Japanese Society for Molecular Imaging, subject number P8-9, May 14, 2009). Further, there have recently been reported compounds usable as a mother nucleus of a red fluorescent probe, which correspond to fluorescein of which 10-oxygen atom of the xanthene ring is structurally modified (Chemical Communications, 47, pp. 4162-4164, 2011).

PRIOR ART REFERENCES

Non-Patent Documents

Non-Patent Document 1: Best, Q et al., Pacifichem 2010, Subject Number 2335, Dec. 19, 2010
Non-Patent Document 2: Yuichiro KOIDE et al., Fourth Convention of The Japanese Society for Molecular Imaging, Subject Number P8-9, May 14, 2009
Non-Patent Document 3; Chemical Communications, 47, pp. 4162-4164, 2011

SUMMARY OF THE INVENTION

Object to be Achieved by the Invention

An object of the present invention is to provide a novel fluorescent probe having a red fluorophore.

More specifically, the object of the present invention is to provide a fluorescent probe that emits red fluorescence by contact with an object substance for measurement by chemically modifying the fluorescein structure.

Means for Achieving the Object

It is known that since the 9-position of the xanthene ring of fluorescein is high electrophilic, nucleophilic attack thereto by the 2'-carboxy group of the benzene ring gives the compound having a spirolactone ring, which is a tautomer, and when fluorescein, which emits strong green fluorescence in the open-ring state, becomes the tautomer having the spirolactone ring, it becomes substantially non-absorptive and non-fluorescent. The inventors of the present invention conducted various researches in order to provide a fluorescent probe that emits red fluorescence by contact with an object substance for measurement by using the aforementioned characteristic in a compound consisting of fluorescein in which the oxygen atom of the 10-position of the xanthene ring is replaced with silicon atom or germanium atom. As a result, they found that compounds represented by the following general formula (I) are very useful as a red fluorescent probe, and accomplished the present invention.

The present invention thus provides a compound represented by the following general formula (I):

[Formula 1]

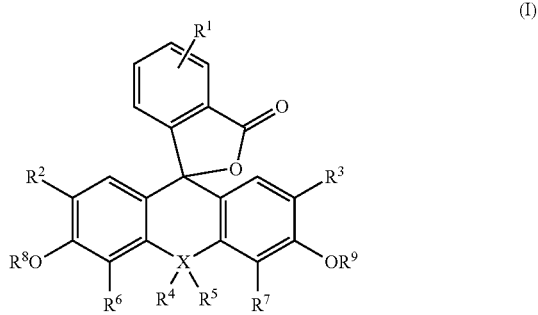

(I)

wherein, in the formula, $R^1$ represents hydrogen atom, or the same or different 1 to 4 monovalent substituents existing on the benzene ring $R^2$ and $R^3$ independently represent hydrogen atom, an alkyl group having 1 to 6 carbon atoms, a halogen atom, or a monovalent hydrophilic substituent; $R^4$ and $R^5$ independently represent an alkyl group having 1 to 6 carbon atoms, or an aryl group having 1 to 6 carbon atoms; $R^6$ and $R^7$ independently represent hydrogen atom, an alkyl group having 1 to 6 carbon atoms, a halogen atom, or a monovalent hydrophilic substituent; $R^8$ and $R^9$, which are the same or different, independently represent hydrogen atom or a monovalent group that is cleaved by contact with an object substance for measurement, provided that $R^8$ and $R^9$ are not simultaneously hydrogen atoms; and X represents silicon atom, germanium atom, or tin atom, or a salt thereof.

According to a preferred embodiment of the aforementioned invention, there is provided the aforementioned compound or a salt thereof, wherein $R^1$ represents hydrogen atom, or 1 to 3 monovalent substituents existing on the benzene ring (the substituents are selected from the group consisting of an alkyl group having 1 to 6 carbon atoms, an alkenyl group having 1 to 6 carbon atoms, an alkynyl group having 1 to 6 carbon atoms, an alkoxy group having 1 to 6 carbon atoms, hydroxy group, carboxy group, sulfonyl group, an alkoxycarbonyl group, a halogen atom, and amino group), $R^2$ and $R^3$ independently represent hydrogen atom, an alkyl group having 1 to 6 carbon atoms, a halogen atom, or a monovalent hydrophilic substituent having an amino group substituted with one or two carboxyalkyl groups (the carboxy groups may form esters) as a partial structure; $R^4$ and $R^5$ independently represent an alkyl group having 1 to 6 carbon atoms, $R^6$ and $R^7$ independently represent hydrogen atom, or a halogen atom, $R^8$ and $R^9$ represent hydrogen atom, or the same monovalent group that is cleaved by contact with an object substance for measurement, provided that $R^8$ and $R^9$ are not simultaneously hydrogen atoms; and X represents silicon atom, According to a further preferred embodiment, there is provided the aforementioned compound or a salt thereof, wherein $R^1$ represents hydrogen atom, or 1 to 3 monovalent substituents existing on the benzene ring (the substituents are selected from the group consisting of an alkyl group having 1 to 6 carbon atoms, an alkoxy group having 1 to 6 carbon atoms, hydroxy group, carboxy group, a halogen atom, and amino group), $R^2$ and $R^3$ independently represent hydrogen atom, or a monovalent hydrophilic substituent having one or two amino groups substituted with two carboxymethyl groups (the carboxy groups may form esters) as partial structures, $R^4$ and $R^5$ independently represent an alkyl group having 1 to 3 carbon atoms, $R^6$ and $R^7$ are both hydrogen atoms, chlorine atoms, or fluorine atoms, $R^8$ and $R^9$ represent hydrogen atom, or a monovalent group that is cleaved by the same reductase, oxidase, or hydrolase, provided that $R^8$ and $R^9$ are not simultaneously hydrogen atoms; and X represents silicon atom.

According to a particularly preferred embodiment of the aforementioned invention, there is provided the aforementioned compound or a salt thereof, wherein $R^1$ represents hydrogen atom, $R^2$ and $R^3$ independently represent hydrogen atom, or an alkyl group having one or two amino groups substituted with two carboxymethyl groups (the carboxy groups may form acetoxymethyl esters) as partial structures (the alkyl group may have oxo group, or contain an amide bond), $R^4$ and $R^5$ independently represent an alkyl group having 1 to 3 carbon atoms, $R^6$ and $R^7$ are both hydrogen atoms, or chlorine atoms, $R^8$ and $R^9$ represent a monovalent group that is cleaved by an enzyme selected from the group consisting of β-lactamase, cytochrome P450 oxidase, β-galactosidase, β-glucosidase, β-glucuronidase, β-hexosaminidase, lactase, alkaline phosphatase, matrix metalloprotease, and glutamyl transferase.

There are also provided a fluorescent probe containing a compound represented by the aforementioned general formula (I) (in the formula, $R^1$, $R^2$, $R^3$, $R^4$, $R^5$, $R^6$, $R^7$, $R^8$, $R^9$, and X have the same meanings as those defined above), or a salt thereof, use of a compound represented by the aforementioned general formula (I) (in the formula, $R^1$, $R^2$, $R^3$, $R^4$, $R^5$, $R^6$, $R^7$, $R^8$, $R^9$, and X have the same meanings as those defined above), or a salt thereof for manufacture of a fluorescent probe, and a method for measuring an object substance for measurement, which comprises the step of contacting a compound represented by the aforementioned general formula (I) (in the formula, $R^1$, $R^2$, $R^3$, $R^4$, $R^5$, $R^6$, $R^7$, $R^8$, $R^9$, and X have the same meanings as those defined above), or a salt thereof with an object substance for measurement, and then measuring fluorescence.

Effect of the Invention

The compounds represented by the general formula (I) and salts thereof provided by the present invention have a characteristic that they give a corresponding compound wherein $R^8$ and $R^9$ are hydrogen atoms by contact with an object substance for measurement such as various enzymes, which then changes into a compound that emits strong red fluorescence due to opening of the intramolecular spirolactone ring. Therefore, the compounds represented by the general formula (I) and salts thereof are useful as a fluorescent probe that enables measurement of various enzymes and the like at high sensitivity.

BRIEF DESCRIPTION OF THE DRAWINGS

The patent or application file contains at least one drawing executed in color. Copies of this patent or patent application publication, with color drawing(s) will be provided by the Office upon request and payment of the necessary fee.

MODES FOR CARRYING OUT THE INVENTION

Figure 1:
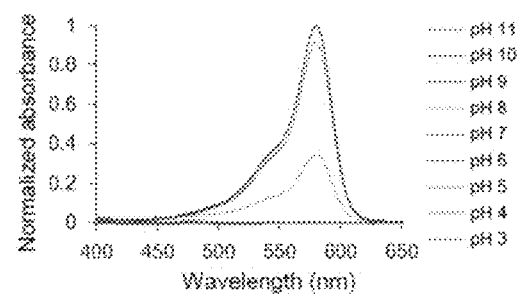
FIG. 1 The upper graph shows pH-dependent changes of absorption spectra of 2-COOH TM (at a concentration of 1 μM in 0.1 M phosphate buffer containing 1% DMSO), and the lower graph shows pH-dependent changes of absorption of 2-COOH TM at 580 nm. In the lower graph, the curves were fitted by single-phase normalization (red) or two-phase normalization (blue), and $X^2$ values were 0.041 and $4.4 \times 10^{-4}$, respectively.
Figure 1:
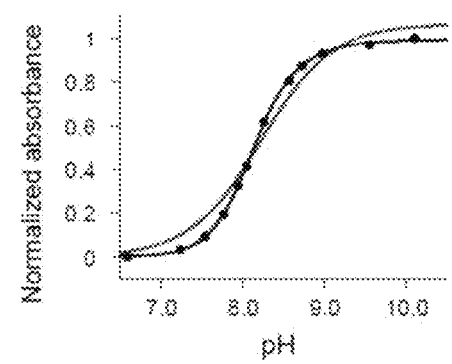
Figure 2:
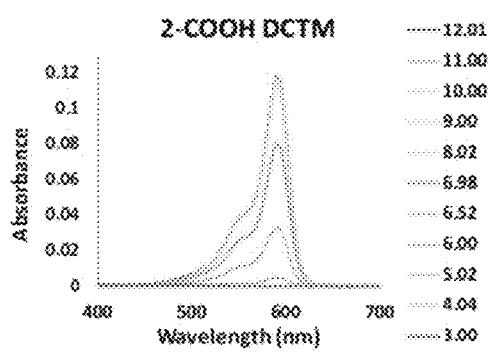
FIG. 2 shows optical characteristics of 2-COOH DCTM and 2-COOH DFTM. The graphs show pH-dependent changes of absorption spectra (left) and fluorescence spectra (right) (at a concentration of 1 μM in 0.1 M phosphate buffer containing 1% DMSO).
Figure 2:
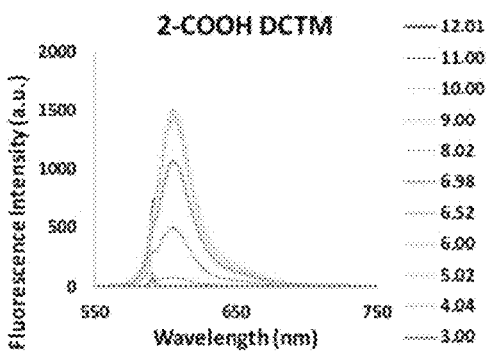
Figure 2:
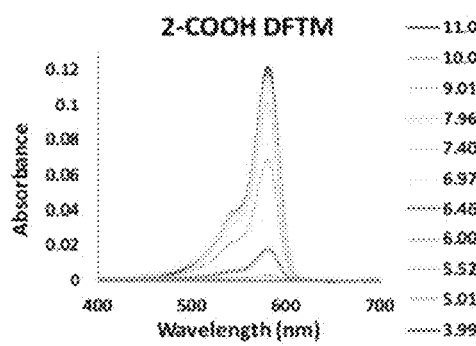
Figure 2:
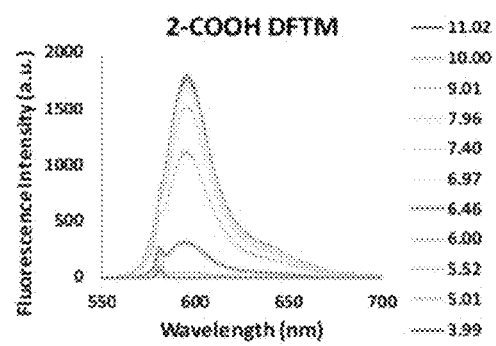

In the specification, "an alkyl group" or an alkyl moiety of a substituent containing an alkyl moiety (for example, an alkoxy group, and the like) means a linear, branched, or cyclic alkyl group, or an alkyl group consisting of a combination thereof, having, for example, 1 to 6 carbon atoms, preferably 1 to 4 carbon atoms, more preferably 1 to 3 carbon atoms, unless specifically indicated. More specifically, examples of the alkyl group include, for example, methyl group, ethyl group, n-propyl group, isopropyl group, cyclopropyl group, n-butyl group, sec-butyl group, isobutyl group, tert-butyl group, cyclopropylmethyl group, n-pentyl group, n-hexyl group, and the like. The "halogen atom" referred to in the specification may be any one of fluorine atom, chlorine atom, bromine atom, and iodine atom, preferably fluorine atom, chlorine atom, or bromine atom, more preferably fluorine atom or chlorine atom, particularly preferably chlorine atom.

In the compound represented by the general formula (I), $R^1$ represents hydrogen atom, or the same or different 1 to 4 monovalent substituents existing on the benzene ring. When $R^1$ represents the monovalent substituents existing on the benzene ring, it is preferred that the same or different about 1 to 3 substituents exist on the benzene ring. When $R^1$ represents one or two or more monovalent substituents, the substituents can substitute at arbitrary positions on the benzene ring. It is preferred that $R^1$ represents hydrogen atom, or one monovalent substituent, and it is more preferred that $R^1$ represents hydrogen atom.

Although type of the monovalent substituent as $R^1$ is not particularly limited, it is preferably selected from, for example, the group consisting of an alkyl group having 1 to 6 carbon atoms, an alkenyl group having 1 to 6 carbon atoms, an alkynyl group having 1 to 6 carbon atoms, an alkoxy group having 1 to 6 carbon atoms, hydroxy group, carboxy group, sulfonyl group, an alkoxycarbonyl group, a halogen atom, and amino group. These monovalent substituents may further have one or two or more arbitrary substituents. For example, the alkyl group as $R^1$ may have one or more of substituents selected from a halogen atom, carboxy group, sulfonyl group, hydroxy group, amino group, an alkoxy group, oxo group, and the like, and the alkyl group as $R^1$ may be, for example, a halogenated alkyl group, a hydroxyalkyl group, a carboxyalkyl group, an aminoalkyl group, or the like. It may contain amide bond in the alkyl chain. The amino group as $R^1$ may have one or two alkyl groups, and the amino group as $R^1$ may be, for example, a monoalkylamino group or a dialkylamino group. Further, when the alkoxy group as by $R^1$ has a substituent, examples thereof include, for example, a carboxy-substituted alkoxy group, an alkoxycarbonyl-substituted alkoxy group, and the like, more specifically, 4-carboxybutoxy group, 4-acetoxymethyloxycarbonylbutoxy group, and the like. Further, when $R^1$ represents one or two or more monovalent substituents, one or two or more of them may be the monovalent hydrophilic substituent explained later for $R^2$ and $R^3$, and when $R^1$ represents a plurality of hydrophilic substituents, they may be the same or different.

$R^2$ and $R^3$ independently represent hydrogen atom, an alkyl group having 1 to 6 carbon atoms, a halogen atom, or a monovalent hydrophilic substituent. When $R^2$ or $R^3$ represents an alkyl group, the alkyl group may have one or two or more substituents selected from a halogen atom, carboxy group, sulfonyl group, hydroxy group, amino group, an alkoxy group, and the like, and the alkyl group as $R^2$ or $R^3$ may be, for example, a halogenated alkyl group, a hydroxyalkyl group, a carboxyalkyl group, or the like. It is preferred that $R^2$ and $R^3$ are independently hydrogen atom or a monovalent hydrophilic substituent, and it is more preferred that one of $R^2$ and $R^3$ is hydrogen atom, and the other is a monovalent hydrophilic substituent.

Although type of the monovalent hydrophilic substituent as $R^2$ and $R^3$ is not particularly limited, the monovalent hydrophilic substituent preferably has an amino group substituted with one or two carboxyalkyl groups as a partial structure. One or more of carboxy groups of the carboxyalkyl group may form an ester. Further, the partial structure is more preferably amino group substituted with two carboxymethyl groups (the carboxy groups may form esters). As the aforementioned ester, an alkyl ester such as ethyl ester, an alkoxyalkyl ester such as methoxymethyl ester, an alkanoloxyalkyl ester such as acetoxymethyl ester, and the like are preferred. In this specification, the term "hydrophilic substituent" includes a substituent that is originally as hydrophilic substituent because of the presence of carboxy group, as well as a substituent that becomes hydrophilic due to generation of carboxy group by hydrolysis of an ester. In the latter case, the substituent forming the ester itself may not be hydrophilic.

As the hydrophilic substituent, for example, an alkyl group having one or two amino groups substituted with one or two carboxyalkyl groups (one or two of carboxy groups of the carboxyalkyl groups may form esters), and the like are preferred. The alkyl group may be substituted with oxo group, and may contain an amide bond, amino group, ether bond, or the like as a constituent of the alkyl chain. Particularly preferred hydrophilic substituents are bis(carboxymethyl)aminomethyl group or an ester thereof, a hydrophilic substituent containing two of bis(carboxymethyl)-aminomethyl groups or esters thereof as partial structures, and the like. As the ester, acetoxymethyl ester is particularly preferred. Examples of the hydrophilic substituent forming an ester include, for example, a hydrophilic substituent having one or two bis (acetoxymethyloxycarbonylmethyl)amino groups, and particularly preferred examples include bis(acetoxymethyloxycarbonylmethyl)aminomethyl group.

$R^4$ and $R^5$ independently represent an alkyl group having 1 to 6 carbon atoms, or an aryl group having 1 to 6 carbon atoms. It is preferred that $R^4$ and $R^5$ are independently an alkyl group having 1 to 3 carbon atoms, and it is more preferred that $R^4$ and $R^5$ are both methyl groups. The alkyl group as $R^4$ or $R^5$ may have one or two or more substituents selected from a halogen atom, carboxy group, sulfonyl group, hydroxy group, amino group, an alkoxy group, and the like, and the alkyl group as $R^4$ or $R^5$ may be for example, a halogenated alkyl group, a hydroxyalkyl group, a carboxyalkyl group or the like. When $R^4$ or $R^5$ represents an aryl group, the aryl group may be a monocyclic aromatic group, or a condensed ring aromatic group, and the aryl ring may contain one or two or more ring-constituting heteroatoms (for example, nitrogen atom, sulfur atom, oxygen atom and the like). As the aryl group, phenyl group is preferred. The aryl ring may have one or two or more substituents on the ring. As the substituents, for example, one or two or more substituents selected from a halogen atom, carboxy group, sulfonyl group, hydroxy group, amino group, an alkoxy group, and the like may exist.

$R^6$ and $R^7$ independently represent hydrogen atom, an alkyl group having 1 to 6 carbon atoms, a halogen atom, or a monovalent hydrophilic substituent. It is preferred that $R^6$ and $R^7$ are both hydrogen atoms, or halogen atoms, it is more preferred that $R^6$ and $R^7$ are both hydrogen atoms, chlorine atoms, or fluorine atoms, and it is particularly preferred that $R^6$ and $R^7$ are both hydrogen atoms, or chlorine atoms.

$R^8$ and $R^9$ represent hydrogen atoms, or independently represent the same or different monovalent groups that are cleaved by contact with an object substance for measurement, provided that $R^8$ and $R^9$ are not simultaneously hydrogen atoms.

Type of the object substance for measurement is not particularly limited, and it may be any of for example, an enzyme, a metal ion (for example, alkali metal ion such as sodium ion and lithium ion, alkaline earth metal ion such as calcium ion, magnesium ion, zinc ion, and the like), a nonmetallic ion (carbonate ion and the like), reactive oxygen species (for example, hydroxy radical, peroxynitrite, hypochlorous acid, hydrogen peroxide, and the like), and the like. The substance is preferably an enzyme.

Examples of the enzyme include, for example, reductase, oxidase, hydrolase, and the like. For example, examples of the enzyme include enzymes useful for diagnosis of infectious diseases and cancers, such as β-lactamase, cytochrome P450 oxidase, β-galactosidase, β-glucosidase, β-glucuronidase, β-hexosaminidase, lactase, alkaline phosphatase, matrix metalloproteinase, glutamyl transferase, and the like, but the enzyme is not limited to these examples. Among the enzymes, hydrolase such as esterase is especially preferred. Typical examples of the hydrolase include, for example, β-galactosidase, β-lactamase, alkaline phosphatase, matrix metalloproteinase, glutamyl transferase, and the like, but hydrolase is not necessarily limited to those mentioned above.

When the object substance for measurement is a hydrolase, the compound of the general formula (I) can be designed so that the compound is hydrolyzed by the enzyme to give a compound wherein both $R^8$ and $R^9$ are hydrogen atoms by choosing a compound or functional group that can serve as a specific substrate of the enzyme. For example, when the object substance for measurement is a saccharide hydrolase, a residue of a saccharide compound that can be a substrate of the enzyme can be used as one or both of $R^8$ and $R^9$. Functional groups of the saccharide compound, such as hydroxy group and amino group, may be protected with appropriate protective groups, if needed. Any of such compounds having a protective group also falls within the scope of the present invention.

When one or both of $R^8$ and $R^9$ are p-aminophenyl group or p-hydroxyphenyl group, the compound is decomposed by contact with a reactive oxygen species to give a compound wherein $R^8$ and $R^9$ are hydrogen atoms, and therefore a reactive oxygen species can be used as the object substance for measurement. Fluorescent probes for reactive oxygen species having p-aminophenyl group or p-hydroxyphenyl group are described in, for example, International Patent Publications WO2001/064664, WO2004/040296, U.S. Pat. No. 7,378,282, and the like.

X represents silicon atom, germanium atom, or tin atom. It is preferably silicon atom or germanium atom, and it is particularly preferably silicon atom.

The compounds represented by the aforementioned general formula (I) may exist as a salt. Examples of the salt include base addition salts, acid addition salts, amino acid salts, and the like. Examples of the base addition salts include, for example, metal salts such as sodium salt, potassium salt, calcium salt and magnesium salt, ammonium salts, and organic amine salts such as triethylamine salt, piperidine salt, and morpholine salt, and examples of the acid addition salts include, for example, mineral acid salts such as hydrochloride, sulfate, and nitrate, and organic acid salts such as methanesulfonate, para-toluenesulfonate, citrate, and oxalate. As the amino acid salt, glycine salt, and the like can be exemplified. However, the salts of the compounds of the present invention are not limited to these examples.

The compounds of the present invention represented by the general formula (I) may have one or two or more asymmetric carbons depending to types of substituents, and they may exist as a stereoisomer such as enantiomer or diastereoisomer. Stereoisomers in pure form, arbitrary mixtures of stereoisomers, racemates, and the like all fall within the scope of the present invention. Further, the compounds of the present invention represented by the general formula (I) and salts thereof may exist as a hydrate or a solvate, and all of these substances are encompassed by the scope of the present invention. Type of the solvent that forms the solvate is not particularly limited, and examples include, for example, such solvents as ethanol, acetone, and isopropanol.

The compounds of the present invention represented by the general formula (I) and salts thereof have a property that they change into a corresponding compound in which $R^8$ and $R^9$ are hydrogen atoms by contact with an object substance for measurement such as various enzymes, and then changes into a compound that emits strong red fluorescence due to formation of an intramolecular spirolactone ring. Therefore, the compounds represented by the general formula (I) and salts thereof are useful as a fluorescent probe that enables measurement of various enzymes and the like at high sensitivity. Further, the compounds having a hydrophilic substituent having bis(acetoxymethyloxycarbonylmethyl)amino group, preferably bis(acetoxymethyloxycarbonylmethy)aminomethyl group, as any one or two or more of $R^1$, $R^2$, $R^3$, $R^6$ and $R^7$ are efficiently incorporated into cells because of high lipophilicity of these substituents, and when they are incorporated into cells, the 4-acetoxymethyloxycarbonylmethyl ester is hydrolyzed by an esterase existing in the cells to generate carboxy group, and thus they are converted into a highly water-soluble compound and stay in the cells for a long period of time. Therefore, they are extremely suitable for imaging of an object substance for measurement in the cells.

Further, when $R^6$ and $R^7$ are both chlorine atoms, after a corresponding compound wherein $R^8$ and $R^9$ are hydrogen atoms is generated by contact with an object substance for measurement such as various enzymes under a physiological neutral condition, the intramolecular spirolactone ring quickly opens, and thus most part of the compound comes to exist as a strongly fluorescent ring-open compound under a neutral condition. Therefore, the compounds wherein both $R^6$ and $R^7$ are chlorine atoms are especially useful as a probe for use under a physiological neutral condition.

The term "measurement" used in this specification should be construed in its broadest sense including, quantification, qualification, as well as measurement, examination, detection, and the like performed for the purposes of diagnosis and the like. The method tot measuring an object substance to measurement utilizing the fluorescent probe of the present invention generally comprises (a) the step of contacting a compound represented by the aforementioned formula (I) with an object substance for measurement to cleave $R^8$ and $R^9$ to generate a corresponding compound wherein both $R^8$ and $R^9$ are hydrogen atoms, and (b) the step of measuring fluorescence of the compound generated in the aforementioned step (a) (the corresponding compound wherein both $R^8$ and $R^9$ are hydrogen atoms, and the intramolecular spirolactone ring has opened). For example, the fluorescent probe of the present invention or a salt thereof can be dissolved in an aqueous medium such as physiological saline and buffer, a mixture of the aqueous medium and a water-miseible organic solvent such as ethanol, acetone, ethylene glycol, dimethyl sulfoxide, and dimethylformamide, or the like, this solution can be added to an appropriate buffer containing cells or tissues, and fluorescence spectrum can be measured before and after contact with the object substance for measurement.

Fluorescence of the compound of which $R^8$ and $R^9$ have been cleaved by the object substance for measurement can be measured by a usual method, and a method of measuring a fluorescence spectrum in vitro, a method of measuring a fluorescence spectrum in vivo by using a bioimaging technique, and the like an be employed. For example, when quantification is performed, it is desirable to create a calibration curve beforehand in a conventional manner.

The fluorescent probe of the present invention may be mixed with additives usually used for preparation of reagents when required, and used as a composition. For example, as additives for using a reagent in a physiological environment, such additives as dissolving aids, pH modifiers, buffering agents, and isotonic agents can be used, and amounts of these can be appropriately selected by those skilled in the art. Such a composition is provided as a composition in an appropriate form such as powdery mixture, lyophilized product, granule, tablet, and solution.

The compounds represented by the general formula (I) can be prepared according to, for example, the preparation method described in Chemical Communications, 47, pp. 4162-4164, 2011. A method for synthesizing the mother nucleus structure is shown in the example section of this specification as a reference example. Further, since specific synthesis methods of typical compounds among the compounds represented by the general formula (I) are described in the examples, those skilled in the art can easily prepare the compounds of the present invention encompassed by the scope of the general formula (I) according to these preparation methods with appropriately changing staring material compounds, reaction conditions, reaction reagents, and the like, if needed.

EXAMPLES

Hereafter, the present invention will be more specifically explained, with reference to examples. However, the scope of the present invention is not limited by the following examples.

Example 1

A preparation intermediate of the compound of the present invention was synthesized according to the following scheme.

[Formula 2]

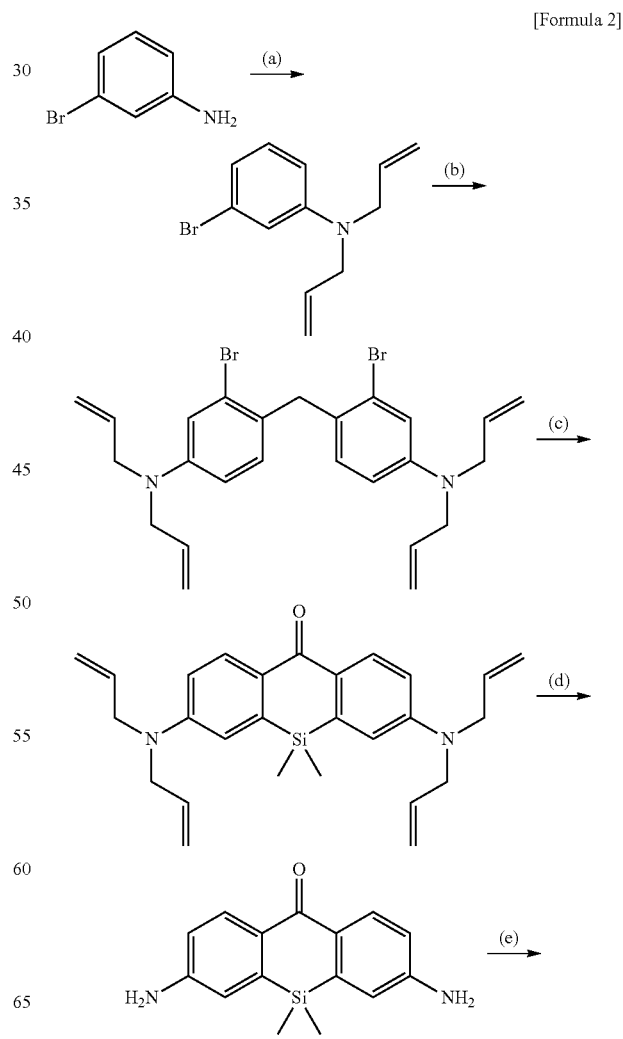

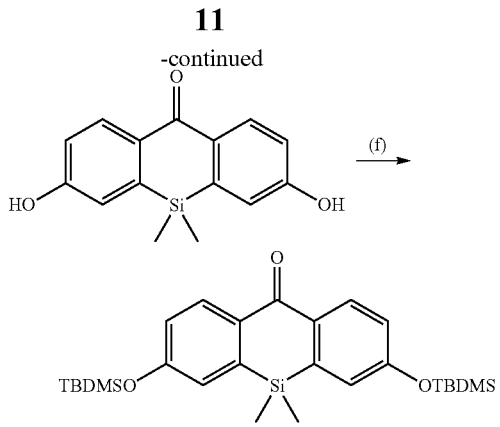

(a) 3-Bromo-N,N-diallylaniline

Potassium carbonate (22.0 g, 159 mmol) was suspended in acetonitrile, the suspension was added with 3-bromoaniline (8.71 mL, 80.0 mmol) and allyl bromide (23.7 mL 280 mmol), and the mixture was stirred at 80° C. for 14 hours. The reaction mixture was cooled to room temperature, then filtered through Celite, and sufficiently washed with ethyl acetate. The solvent was removed, and then the residue was purified by column chromatography (silica gel, ethyl acetate/hexane (1/40)) to obtain 3-bromo-N,N-diallylaniline (17.1 g, 67.9 mmol, yield 85%).

$^1$H-NMR (300.40 MHz, CDCl$_8$): δ 3.87-3.90 (m, 4H), 5.11-5.15 (m, 2H), 5.17-5.18 (m, 2H), 5.75-5.88 (m, 2H), 6.58 (dd, 1H, J=2.2, 8.1 Hz), 6.77-6.81 (m. 2H), 7.01 (t, 1H, J=8.1Hz)

$^{13}$C-NMR (75.45 MHz, CDCl$_8$): δ 52.7, 110.8, 115.0, 116.3, 119.0, 123.3, 130.2, 133.2, 150.0

HRMS (ESI+): Found 252.0429, calculated 252.0388 for [M+H]$^+$ (4.1 mmu)

(b) Bis(2-bromo-4-N,N-diallylaminophenyl)methane

3-Bromo-N,N-diallylaniline (17.1 g, 67.9 mmol) was dissolved in acetic acid (200 mL), the solution was added with a 37% formaldehyde solution (10.2 g, 340 mmol), and the mixture was heated at 80° C. for 75 minutes. The reaction mixture was cooled to room temperature, and then neutralized with saturated aqueous sodium hydrogencarbonate and sodium hydroxide. This mixture was extracted with dichloromethane, and the organic layer was washed with brine. The organic layer was dried over sodium sulfate, the solvent was removed, and then the residue was purified by column chromatography (silica gel, ethyl acetate/hexane (1/30)) to obtain bis(2-bromo-4-N,N-diallylaminophenyl)methane (15.2 g, 29.5 mmol, yield 87%).

$^1$H-NMR (300.40 MHz, CDCl$_8$): δ 3.85-3.87 (m, 8H), 3.96 (s, 2H), 5.13-5.19 (m, 8H), 5.76-5.88 (m, 4H), 6.54 (dd, 2H, J=2.9, 8.8 Hz), 6.81 (d, 2H, J=8.1 Hz), 6.90 (d, 2H, J=2.9 Hz $^{13}$C-NMR (75.45 MHz, CDCl$_8$): δ 39.7, 52.7, 111.7, 116.0, 116.2, 125.5, 126.9, 130.8, 133.5, 148.1

HRMS (ESI+): Found 517.0654, calculated 517.0677 for [M+H]$^+$ (−2.3 mmu)

(c) N,N,N',N'-Tetraallyl-diamino-Si-xanthone

Bis(2-bromo-4-N,N-diallylaminophenyl)methane (8.16 g, 15.8 mmol) and anhydrous tetrahydrofuran (THF, 50 mL) were put into a dried flask inside of which was substituted with argon. The mixture was cooled to −78° C., and then added with 1 M sec-butyllithium (45 mL, 45 mmol), and the mixture was stirred for 20 minutes. The mixture was slowly added with dichlorodimethylsilane (2.9 mL, 30 mmol) dissolved in anhydrous THF (10 mL) at the same temperature, and the mixture was returned to room temperature, and stirred for 1 hour, The reaction was terminated with 2 N hydrochloric acid, and the reaction mixture was neutralized with sodium hydrogencarbonate. This mixture was extracted with dichloromethane, the organic layer was washed with brine, and dried over sodium sulfate, and then the solvent was removed. The residue was dissolved in acetone (150 mL), the solution was cooled to 0° C. and added portionwise with potassium permanganate (6.88 g, 43.5 mmol) over 2 hours, and the mixture was further stirred at the same temperature for 1 hour. The mixture was added with dichloromethane (200 mL), and the mixture was subjected to suction filtration using filter paper. The solvent was removed, and the residue was purified by column chromatography (silica gel, dichloromethane) to obtain N,N,N',N'-tetraallyl-diamino-Si-xanthone (2.23 g, 5.20 mmol, yield 33%).

$^1$H-NMR (300.40 MHz, CDCl$_8$): δ 0.41 (s, 6H), 4.02 (d, 8H, J=5.1 Hz), 5.17-5.23 (m, 8H), 5.82-5.94 (m, 4H), 6.80-6.83 (m, 4H), 8.34 (d, 2H, J=8.1 Hz)

$^{13}$C-NMR (75.45 MHz, CDCl$_8$): δ 1.1, 52.8, 113.5, 114.8, 116.7, 130.0, 131.7, 133.1, 140.5, 150.2, 185.1

HRMS (ESI+): Found 429.2347, calculated 429.2362 for [M+H]$^+$ (−1.5 mmu)

(d) Diamino-Si-xanthone

Tetrakis(triphenylphosphine)palladium (Pd(PPh$_3$)$_4$, 35.0 mg, 0.0303 mmol) and 1,3-dimethylbarbituric acid (196 mg, 1.08 mmol) were put into a dried flask inside of which was substituted with argon. The mixture was added with N,N,N',N'-tetraallyl-diamino-Si-xanthone (99.2 mg, 0.231 mmol) dissolved in dichloromethane (10 mL), and the mixture was stirred at 64° C. for 16 hours. The solvent was removed, the residue was suspended in saturated aqueous sodium carbonate, and the suspension was extracted with dichloromethane. The organic layer was dried over sodium sulfate, the solvent was removed, and then the residue was purified by column chromatography (silica gel, ethyl acetate/hexane (4/3)) to obtain diamino-Si-xanthone (48.8 mg, 0.182 mmol, yield 79%).

$^1$H-NMR (300.40 MHz, CD$_3$OD): δ 0.40 (s, 6H), 6.76 (dd, 2H. J=2.6, 8.4 Hz), 6.88 (d, 2H, J=2.2 Hz), 8.13 (d, 2H, J=8.8 Hz)

$^{13}$C-NMR (75.45 MHz, CD$_3$OD): δ −1.3, 116.6, 118.4, 131.0, 132.8, 142.6, 153.0, 187.5

HRMS (ESI+Tof): m/z Found 269.1108, calculated 269.1110 for [M+H]$^+$ (−0.2 mmu)

(e) Dihydroxy-Si-xanthone

Diamino-Si-xanthone (48.8 mg, 0.182 mmol) was dissolved in a mixed solvent (methanol, 6 N H$_2$SO$_4$, 4/5, 45 mL). The solution was cooled to 0°C., and then slowly added with sodium nitrite (84.6 mg, 1.22 mmol) dissolved in water (2 mL), and the mixture was stirred at the same temperature for 1 hour. This mixture was slowly added to boiling 1 N H$_2$SO$_4$ (50 mL), and the mixture was further refluxed for 10 minutes, and then cooled on ice. The reaction mixture was extracted with dichloromethane, and the organic layer was sufficiently washed with brine. The organic layer was dried over sodium sulfate, the solvent was removed, and then the residue was purified by column chromatography (silica gel, methanol/dichloromethane (1/20)) to obtain dihydroxy-Si-xanthone (32.9 mg, 0.122 mmol, yield 67%).

$^1$H-NMR (300.40 MHz, CD$_3$OD): δ 0.45 (s, 6H), 6.95 (dd, 2H, J=2.2, 8.8 Hz), 7.07 (d, 2H, J=2.2 Hz), 8.26 (d, 2H, J=8.8 Hz)

$^{13}$C-NMR, (75.45 MHz, CD$_3$OD): δ −1.5, 118.4, 120.0, 133.3, 133.8, 143.1, 162.2, 187.6

HRMS (ESI-Tof): Found 269.0674, calculated 269.0634 for [M−H] (4.0 mmu)

(f) 3,6-Di-tert-butyldimethylsilyloxy-Si-xanthone

Dihydroxy-Si-xanthone (32.9 mg, 0.122 mmol) and imidazole (85.5 mg, 1.26 mmol) were dissolved in dichloromethane (20 mL), the solution was slowly added with tert-butyldimethylsilyl chloride (TBDMSCl, 185 mg, 1.23 mmol) dissolved in dichloromethane (5 mL), and the mixture was stirred at room temperature for 14 hours. The mixture was added with water, the mixture was extracted with dichloromethane, and the organic layer was washed with brine. The organic layer was dried over sodium sulfate, the solvent was removed, and then the residue was purified by column chromatography (silica gel, ethyl acetate/hexane (1/20)) to obtain 3,6-di-tert-butyldimethylsilyloxy-Si-xanthone (52.8 mg, 0.106 mmol, yield 84%).

$^1$H-NMR (300.40 MHz, CDCl$_8$): δ 0.26 (s, 12H), 0.46 (s, 6H), 1.01 (s, 18H), 6.98 (dd, 2H, J=2.2, 8.8 Hz), 7.04 (d, 2H, J=2.9 Hz), 8.37 (d, 2H, J=8.8 Hz)

$^{13}$C-NMR (75.45 MHz, CDCl$_8$): δ −4.3, −1.6, 18.3, 25.6, 121.8, 123.7, 132.3, 134.5, 141.1, 158.7, 186.0

HRMS (ESI+): Found 499.2480, calculated 499.2520 for [M+]$^+$ (4.0 mmu)

Example 2

A germanium-containing compound as a preparation intermediate of the compound of the present invention was synthesized according to the following scheme.

[Formula 3]

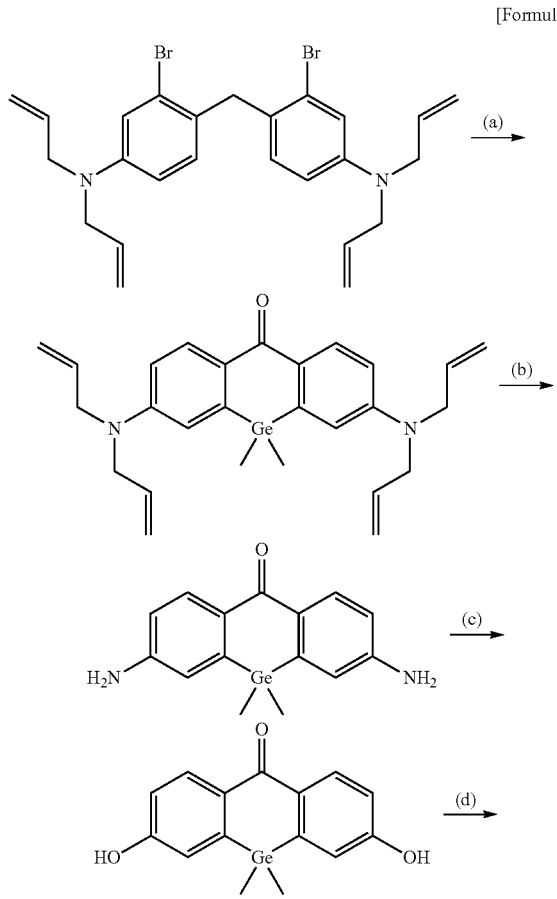

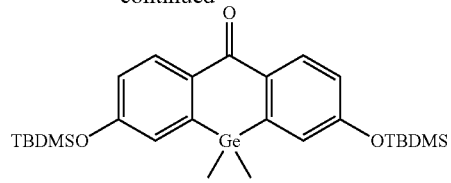

(a) N,N,N',N'-3,6-Tetraallyl-diamino-Ge-xanthone

Bis(2-bromo-4-N,N-diallylaminophenyl)methane (6.16 g, 11.9 mmol) and anhydrous THF (40 mL) were put into a dried flask inside of which was substituted with argon. The mixture was cooled to −78° C., and then added with 1 M sec-butyl-lithium (BuLi, 34 mL, 34 mmol), and the mixture was stirred for 20 minutes. The mixture as slowly added with dichlorodimethylgermane (2.62 mL, 22.7 mmol) dissolved in anhydrous THF (15 mL) at the same temperature, and the mixture was returned to room temperature, and stirred for 1 hour. The reaction was terminated with 2 N hydrochloric acid, and the reaction mixture was neutralized with sodium hydrogencarbonate. This mixture was extracted with dichloromethane, the organic layer was washed with brine, and dried over sodium sulfate, and then the solvent was removed. The residue was dissolved in acetone (120 mL), the solution was cooled to 0° C., and added portionwise with potassium permanganate (5.20 g, 32.9 mmol) over 2 hours, and the mixture was further stirred at the same temperature for 1 hour. The mixture was added with dichloromethane (200 mL), and the mixture was subjected to suction filtration using filter paper. The solvent was removed, and the residue was purified by column chromatography (silica gel, dichloromethane) to obtain the objective compound (1.29 g, 2.72 mmol, yield 23%).

$^1$H NMR (300 MHz, CDCl$_8$): δ 0.54 (s, 6H), 4.00-4.02 (m., 8H), 5.17-5.23 (m, 8H), 5.81-5.94 (m, 4H), 6.72 (d, 2H, J=2.9 Hz), 6.78 (dd, 2H, J=2.6, 9.2 Hz), 8.36 (d, 2H, J=8.8 Hz)

$^{13}$C NMR (75 MHz, CDCl$_8$): δ −1.8, 52.3, 112.6, 114.4, 116.2, 129.6, 131.7, 132.7, 142.8, 149.8, 184.5

LRMS (ESI$^+$): m/z Found 475, calculated 475 for [M+H]$^+$

(b) 3,6-Diamino-Ge-xanthone

Pd(PPh$_3$)$_4$ (330 mg, 0.285 mmol) and 1,3-dimethylbarbituric acid (1.41 g, 9.04 mmol) were put into a dried flask inside of which was substituted with argon. The mixture was added with N,N,N',N'-tetraallyldiamino-Ge-xanthone (1.00 g, 2.11 mmol) dissolved in dichloromethane (50 mL), and the mixture was stirred at 35° C. for 16 hours. The solvent was removed, the residue was suspended in saturated aqueous sodium carbonate, and the suspension was extracted with dichloromethane. The organic layer was dried over sodium sulfate, the solvent was removed, and then the residue was purified by column chromatography (silica gel, ethyl acetate/hexane (4/3)) to obtain a 3,6-diamino-Ge-xanthone mixture (760 mg, yield quantitative).

$^1$H NMR (300 MHz, CD$_3$OD): δ 0.55 (s, 6H), 6.73-6.76 (m, 4H), 8.33 (d, 2H, J=9.5 Hz)

$^{13}$C NMR (75 MHz, CD$_3$OD): δ −1.9, 116.1, 118.3, 130.9, 133.2, 145.2, 152.9, 187.3

LRMS (ESI$^+$): m/z Found: 315, calculated 315 for [M+H]$^+$

(c) 3,6-Dihydroxy-Ge-xanthone

The 3,6-diamino-Ge-xanthone mixture (760 mg) was dissolved in a mixture of methanol and 6 N H$_2$SO$_4$ (3/4, 45 mL). The solution was cooled to 0° C., and then slowly added with sodium nitrite (838 mg, 12.1 mmol) dissolved in water (5 mL), and the mixture was stirred at the same temperature for 1 hour. This mixture was slowly added to boiling 1 N H$_2$SO$_4$ (70 mL), and the mixture was further refluxed for 10 minutes, and then cooled on ice. The reaction mixture was extracted with dichloromethane, and the organic layer was sufficiently washed with brine. The organic layer was dried over sodium sulfate, the solvent was removed, and then the residue was purified by column chromatography (silica gel, ethyl acetate/hexane (1/1)) to obtain 3,6-dihydroxy-Ge-xanthone (478 mg, 1.52 mmol, yield 56% (two steps)).

$^1$H NMR (300 MHz, CD$_3$OD): δ 0.58 (s, 6H), 6.90 (dd, 2H, J=2.2, 8.8 Hz), 7.0 (d, 2H, J =2.2 Hz), 8.25 (d, 2H, J=8.8 Hz)

$^{13}$C NMR (75 MHz, (CD$_3$OD): δ –2.0, 117.7, 120.0, 133.7, 133.8, 145.6, 162.0, 187.7

LRMS (ESI$^+$): Found 317, calculated 317 for [M+]$^+$ (d) 3,6-DiTBDMSO-Ge-xanthone Dihydroxy-Ge-xanthone (478 mg, 1.52 mmol) and imidazole (1.77 g, 26.0 mmol) were dissolved in dichloromethane (150 mL), the solution was slowly added with tert-butyldimethylsilyl chloride (TBDMSCl, 3.70 g, 24.5 mmol) dissolved in dichloromethane (50 mL), and the mixture was stirred at room temperature for 14 hours. The mixture was added with water, the mixture was extracted with dichloromethane, and the organic layer was washed with brine. The organic layer was dried over sodium sulfate, the sol vent was removed, and then the residue was purified by column chromatography (silica gel, ethyl acetate/hexane (1/30)) to obtain 3,6-diTBDMSO-Ge-xanthone (702 mg, 1.29 mmol, yield 85%).

$^1$H NMR (300 MHz, CDCl$_8$): δ 0.25 (s, 12H), 0.59 (s, 6H), 1.01 (s, 18H), 6.92-6.98 (d, 4H, m), 8.36 (d, 2H, J=8.1 Hz)

$^{13}$C NMR (75 MHz, CDCl$_8$): δ –4.4, –1.6, 18.2, 25.8, 121.1, 123.7, 132.5, 134.6, 143.6, 158.6, 185.9

LRMS (ESI$^+$): m/z Found 545, calculated 545 for [M+H]$^+$

Example 3

A preparation intermediate of the compound of the present invention, wherein R$^4$ and R$^5$ are ethyl groups, was synthesized according to the following scheme.

[Formula 4]

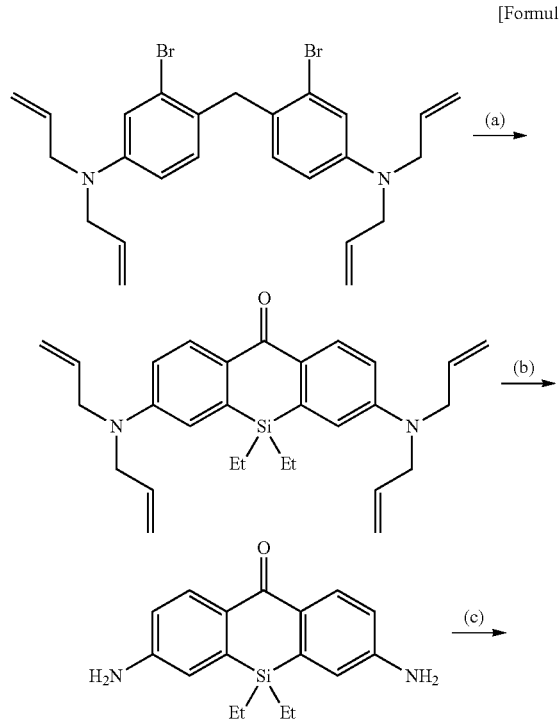
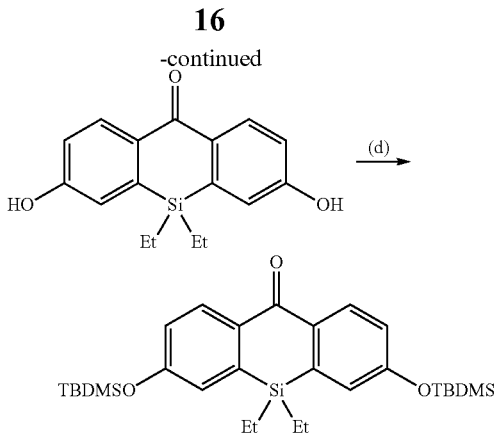

(a) N,N,N',N'3,6-Tetraallyldiamino-diethyl-Si-xanthone

Bis(2-bromo-4-N,N-diallylaminophenyl)methane (1.65 g, 3.20 mmol) and anhydrous THF (20 mL) were put into a dried flask inside of which was substituted with argon. The mixture was cooled to –78° C., and then added with 1 M sec-BuLi (10 mL, 10 mmol)), and the mixture was stirred for 20 minutes. The mixture was slowly added with diethyldichlorosilane (SiEt$_2$Cl$_2$, 1.04 mL, 7.02 mmol, Et represents ethyl group) dissolved in anhydrous THF (5 mL) at the same temperature, and the mixture was returned to room temperature, and stirred for 1 hour. The reaction was terminated with 2 N hydrochloric acid, and the reaction mixture was neutralized with sodium hydrogencarbonate. This mixture was extracted with dichloromethane, the organic layer was washed with brine, and dried over sodium sulfate, and then the solvent was removed. The residue was dissolved in acetone (50 mL), the solution was cooled to 0° C. and added portionwise with potassium permanganate (1.49 g. 9.43 mmol) over 2 hours, and the mixture was further stirred at the same temperature for 1 hour. The mixture was added with dichloromethane (50 mL), and the mixture was filtered through Celite. The solvent was removed, and the residue as purified by column chromatography (silica gel, hexane/ethyl acetate (10/1)) to obtain N,N,N',N'-3,6-tetraallyldiamino-diethyl-Si-xanthone (419 mg, 0.917 mmol, yield 29%).

$^1$H NMR (300 MHz, CDCl$_8$): δ 0.91 (s, 10H), 4.01-4.02 (m, 8H), 5.17-5.22 (m, 8H), 5.82-5.94 (m, 4H), 6.79-6.84 (m, 4H), 8.35 (d, 2H, J=8.8 Hz)

$^{13}$C NMR (75 MHz, CDCl$_8$)L: δ 5.56, 7.48, 52.7, 113.3, 115.0, 116.5, 130.9, 131.6, 133.1, 138.3, 149.9, 185.3

HRMS (ESI$^+$): m/z Found 457.2661, calculated 457.2675 for [M+H]$^+$ (–1.5 mmu)

(b) 3,6-Diamino-diethyl-Si-xanthone

Pd(PPh$_3$)$_4$ (204 mg, 0.176 mmol) and 1,3-dimethylbarbituric acid (1.04 g, 6.67 mmol) were put into a dried flask inside of which was substituted with argon. The mixture was added with N,N,N',N'-tetraallyldiamino-diethyl-Si-xanthone (419 mg, 0.917 mmol) dissolved in dichloromethane (30 mL), and the mixture was stirred at 35° C. for 16 hours. The solvent was removed, the residue was suspended in saturated aqueous sodium carbonate, and the suspension was extracted with dichloromethane. The organic layer was dried over sodium sulfate, the solvent was removed, and then the residue was purified by column chromatography (silica gel, ethyl acetate/hexane (4/5)) to obtain 3,6-diamino-diethyl-Si-xanthone (236 mg, 0.796 mmol, yield 87%).

$^1$H NMR (300 MHz, CDCl$_8$): δ 0.83-0.95 (m, 10H), 4.10 (s, 4H), 6.76-6.81 (m, 4H), 8.33 (d, 2H, J=7.8 Hz)

$^{13}$C NMR (75 MHz, CDCl$_8$): δ 5.37, 7.38, 116.2, 117.5, 132.0, 132.9, 138.8 148.9, 185.5

(c) 3,6-Dihydroxy-diethyl-Si-xanthone

The 3,6-Diamino-diethyl-Si-xanthone mixture (236 mg, 0.796 mmol) was dissolved in a mixture of methanol and 6 N sulfuric acid (3/4, 35 mL). The solution was cooled to 0° C., and then slowly added with sodium nitrite (315 mg, 4.56 mmol) dissolved in water (3 mL), and the mixture was stirred at the same temperature for 1 hour. This mixture was slowly added to boiling 1 N sulfuric acid (50 mL), and the mixture was further refluxed for 10 minutes, and then cooled on ice. The reaction mixture was extracted with dichloromethane, and the organic layer was sufficiently washed with brine. The organic layer was dried over sodium sulfate, the solvent was removed, and then the residue was purified by column chromatography (silica gel, ethyl acetate/hexane (1/1)) to obtain 3,6-dihydroxy-diethyl-Si-xanthone (74.3 mg, 0.249 mmol, yield 31%).

$^1$H NMR (300 MHz, CD$_3$OD): δ 0.83-1.04 (m, 10H), 6.99 (dd, 2H, J=2.2, 8.8 Hz), 7.09 (d, 2H, J=2.9 Hz), 8.31 (d, 2H, J=8.8 Hz)

$^{13}$C NMR (75 MHz, CD$_3$OD): δ 6.07, 7.56, 118.4, 120.0, 133.4, 135.0, 140.9, 162.0, 187.9

HRMS (ESI$^+$): m/z Found 321.0964, calculated 321.0923 for [M+Na]$^+$ (4.1 mmu)

(d) 3,6-DiTBDMSO-diethyl-Si-xanthone

Dihydroxy-diethyl-Si-xanthone (74.3 mg, 0.249 mmol) and imidazole (326 mg, 4.79 mmol) were dissolved in dichloromethane (20 mL), the solution was slowly added with TIB-DMSCl (715 mg, 4.74 mmol) dissolved in dichloromethane (5 mL), and the mixture was stirred at room temperature for 14 hours. The mixture was added with water, the mixture was extracted with dichloromethane, and the organic layer was washed with brine. The organic layer was dried over sodium sulfate, the solvent was removed, and then the residue was purified by column chromatography (silica gel, ethyl acetate/hexane (1/30)) to obtain 3,6-diTBDMSO-diethyl-Si-xanthone (93.2 mg, 0.177 mmol, yield 71%).

$^1$H NMR, (300 MHz, CDCl$_8$): δ 0.26 (s, 12H), 0.85-1.02 (m, 28H), 6.98-7.05 (m, 4H), 8.39 (d, 2H, J=8.1 Hz)

$^{13}$C NMR (75 MHz, CDCl$_8$): δ 4.14, 5.46, 7.45, 18.5, 25.8, 122.1, 123.9, 132.5, 135.8, 139.2, 158.7, 186.3

HRMS (ESI$^+$): m/z Found 527.2809, calculated 527.2833 for [M+H]$^+$ (3.6 mmu)

Example 4

(e) Synthesis of Compound Represented by the General Formula (I) (General Procedure)

A 2-bromobenzoic acid ester and anhydrous THF are put into a dried flask inside of which has been substituted with argon. The mixture is cooled to −78° C., and then added with 1 M sec-BuLi (0.5 mmol), and the mixture is stirred for 20 minutes. The mixture is slowly added with 3,6-diOTBDMS-X-xanthone dissolved in anhydrous THF at the same temperature, and the mixture is returned to room temperature. The mixture is stirred at room temperature for 1 hour, and then added with 2 N hydrochloric acid (10 mL), and the mixture is stirred for 20 minutes. The mixture is extracted With dichloromethane, and the organic layer is washed with brine, and dried over sodium sulfate. The solvent is removed, and then the residue is purified by HPLC to obtain a compound represented by the general formula (I).

(b) Synthesis of 2-COOH TM

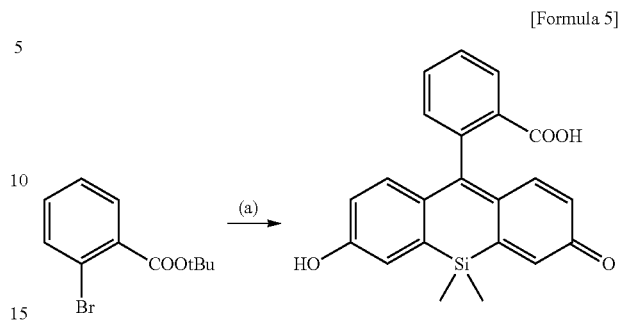

[Formula 5]

tert-Butyl 2-bromobenzoate (800 mg, 3.11 mmol) and anhydrous THF (5 mL) were put into a dried flask inside of which was substituted with argon. The mixture was cooled to −78° C., and then added with 1 M sec-BuLi (2.0 mmol), and the mixture was stirred for 20 minutes. The mixture was slowly added with 3,6-diOTBDMS-Si-xanthone (40.0 mg, 0.0802 mmol) dissolved in anhydrous THF (5 mL) at the same temperature, and the mixture was returned to room temperature. The mixture was stirred at room temperature for 30 minutes, and then added with 2 N hydrochloric acid (10 mL), and the mixture was stirred for 20 minutes. The mixture was extracted with dichloromethane, and the organic layer was washed with brine, and dried over sodium sulfate. The solvent was removed, then the residue was added with trifluoroacetic acid (TFA, 3 mL), and the mixture was stirred at room temperature for 1 hour. The solvent was removed, and then the residue was purified by HPLC to obtain 2-COOH TM (13.6 mg, 0.0358 mmol, yield 45%).

$^1$H-NMR (300 MHz CD$_3$COCD$_3$): δ 0.56 (s, 3H), 0.64 (s, 3H), 6.76 (dd, 2H J=2.9, 8.8 Hz), 6.83 (d, 2H, J=8.8 Hz), 7.23 (d, 2H J=2.9 Hz), 7.38 (d 1H, J=7.3 Hz), 7.67 (td, 1H, J=1.5, 7.3 Hz), 7.80 (td, 1H, J=1.5, 7.3 Hz). 7.94 (dd, 1H, J=1.5, 7.3 Hz)

$^{13}$C-NMR (100 MHz, CD$_3$COCD$_3$): δ −1.4, 0.2, 91.1, 117.6, 121.1, 125.5, 126.3, 127.0, 129.3, 130.1, 135.1, 136.7, 138.2, 155.3, 157.7, 170.4

HRMS (ESI$^+$): m/z Found 375.1018, calculated 375.1053 for [M+H]$^+$ (−3.5 mmu)

Example 5

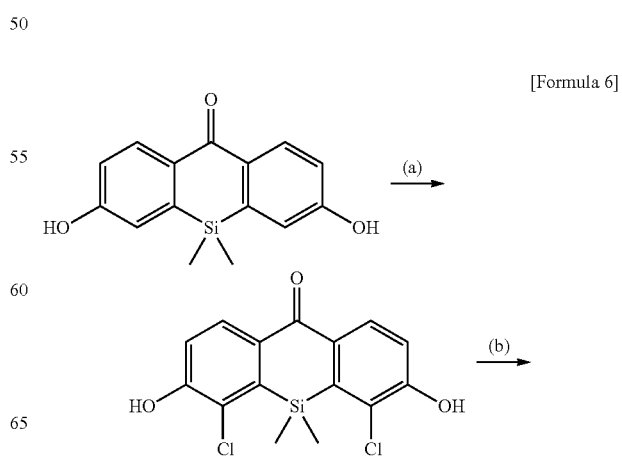

[Formula 6]

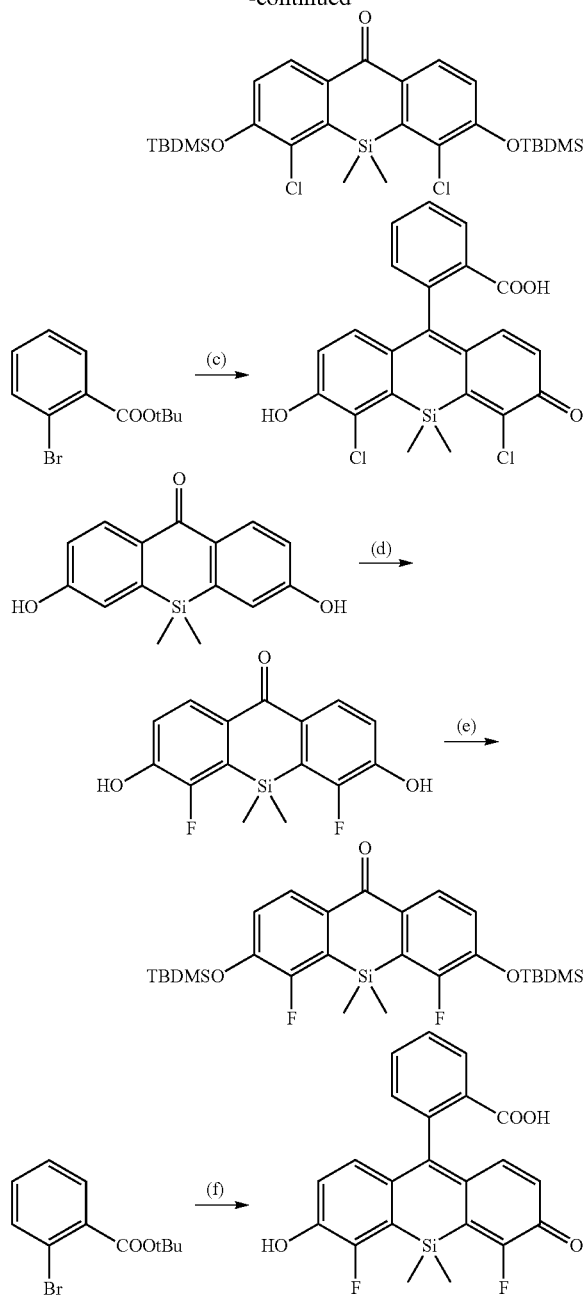

(a) 4,5-Dichloro-3,6-dihydroxy-Si-xanthone 3,6-Dihydroxy-Si-xanthone (81.1 mg, 0.300 mmol) was dissolved in methanol (5 mL), the solution was slowly added with 0.1 N sodium hydroxide (4 mL) in which sodium hypochlorite (NaOCl) was dissolved at 100 mM, and the mixture was stirred at room temperature for 1 hour. The reaction mixture was adjusted to pH 2 by addition of 2 N hydrochloric acid, and then extracted with ethyl acetate, and the organic layer was washed with brine. The organic layer was dried over sodium sulfate, the solvent was removed, and then the residue was purified by column chromatography (silica gel, ethyl acetate/hexane (1/1)) to obtain 4,5-dichloro-3,6-dihydroxy-Si-xanthone (83.8 mg, 0.247 mmol, yield 82%).

$^1$H-NMR (400 MHz, CD$_3$OD): δ 0.80 (s, 1H), 7.11 (d, 2H, J=8.8 Hz), 8.27 (d, 2H, J=8.8 Hz)

$^{13}$C-NMR (100 MHz, CD$_3$OD): δ −1.6, 119.0, 127.0, 132.0, 133.8, 141.4, 158.4, 186.0

HRMS (ESI$^+$): m/z Found 339.0053, calculated 339.0011 for [M+H]$^+$ (4.2 mmu)

(b) 4,5-Dichloro-3,6-diOTBDMS-Si-xanthone 4,5-Dichloro-3,6-dihydroxy-Si-xanthone (69.0 mg, 0.203 mmol), and imidazole (54.5 mg, 0.801 mmol) were dissolved in dichloromethane (10 mL), the mixture was slowly added with TBDMSCl (121 mg, 0.803 mmol), and the mixture was stirred overnight at room temperature. The solvent was removed, and then the residue was purified by column chromatography (silica gel, dichloromethane) to obtain 4,5-dichloro-3,6-diOTBDMS-Si-xanthone (109 mg, 0.193 mmol, yield 95%).

$^1$H-NMR (400 MHz, CDCl$_3$): δ 0.30 (s, 12H), 0.81 (s, 6H), 1.06 (s, 18H), 7.06 (d, 2H, J=. 8.8 Hz), 8.35 (d, 2H, J=8.8 Hz)

$^{13}$C-NMR (100 MHz, CDCl$_8$): δ −4.3, −2.0, 18.4, 25.6, 121.5, 130.6, 131.0, 134.2, 140.5, 155.1, 184.9

HRMS (ESI$^+$): m/z Found 567.1731, calculated 567.1740 for [M+H]$^+$ (−0.9 mmu)

(c) 4',5'-Dichloro-2-COOH TokyoMagenta (2-COOH DCTM)

tert-Butyl 2-bromobenzoate (129 mg, 0.502 mmol) and anhydrous THF (5 mL) were put into a dried flask inside of which was substituted with argon. The mixture was cooled to −78° C., and then added with 1 M sec-BuLi (0.30 mmol), and the mixture was stirred for 20 minutes. The mixture was slowly added with 4,5-dichloro-3,6-diOTBDMS-Si-xanthone (11.3 mg, 0.0200 mmol) dissolved in anhydrous THF (5 mL) at the same temperature, and the mixture was returned to room temperature. The mixture was stirred at room temperature for 1 hour, and then added with 2 N hydrochloric acid (10 mL), and the mixture was stirred for 20 minutes. The mixture was extracted with dichloromethane, and the organic layer was washed with brine, and dried over sodium sulfate, The solvent was removed, then the residue was added with TFA (5 mL), and the mixture was stirred at room temperature for 2 hours. The solvent was removed, and then the residue was purified by HPLC to obtain 2-COOH DCTM (5.7 mg, 0.013 mmol, yield 64%).

$^1$H-NMR (400 MHz, CD$_3$OD): δ 0.83 (s, 3H), 0.98 (s, 3H), 6.85 (d, 2H J=8.8 Hz), 6.89 (d, 2H, J=8.8 Hz), 6.98 (d, 1H J=7.8 Hz), 7.51 (td, 1H, J=1.0, 7.6 Hz), 7.60 (td, 1H, J=1.0, 7.6 Hz), 7.90 (d, 1H, J=7.8 Hz)

$^{13}$C-NMR (100 MHz, CD$_3$COCD$_3$): δ 0.2, 0.5, 90.0, 119.8, 123.6, 124.3, 126.4, 127.1, 127.8, 129.9, 135.1, 136.2, 136.7, 153.6, 158.3, 171.2

HRMS (ESI$^+$): m/z Found 443.0241, calculated 443.0273 for [M+H]$^+$ (−3.2 mmu)

(d) 4,5-Difluoro-3,6-dihydroxy-Si-xanthone 3,6-Dihydroxy-Si-xanthone (13.5 mg, 0.050 mmol) was dissolved in acetonitrile (3 mL), the solution was added with Selectfluor (registered trade mark, 35.4 mg, 0.1 mmol), and the mixture was refluxed overnight by heating at 80° C., and then purified by HPLC to obtain 4,5-difluoro-3,6-dihydroxy-Si-xanthone (4.1 mg, 0.013 mmol, yield 27%).

$^1$H-NMR (400 MHz, CD$_3$OD):δ 0.62-0.63 (m, 6H), 7.12 (m, 2H), 8.13 (d, 2H, J=8.8 Hz)

HRMS (ESI$^+$): m/z, Found 329.0393, calculated 329.0422 for [M+Na]$^+$ (−2.9 mmu)

(e) 4,5-Difluoro-3,6-diOTBDMS-Si-xanthone 4,5-Difluoro-3,6-dihydroxy-Si-xanthone (3.1 mg, 0.010 mmol) and imidazole (6.8 mg, 0.10 mmol) were dissolved in dichloromethane (2 mL), the solution was slowly added with TBDMSCl (15.1 mg, 0.10 mmol), and the mixture was stirred overnight at room temperature. The solvent was removed, and then the residue was purified by column chromatography (silica gel, dichloromethane) to obtain 4,5-difluoro-3,6-di-OTBDMS-Si-xanthone (4.7 mg, 0.088 mmol, yield 88%).

$^1$H-NMR (400 MHz, CDCl$_3$): δ 0.25 (s, 12H), 0.64 (s, 6H), 1.02 (s, 18H), 7.09 (t, 2H, J=8.8 Hz), 8.20 (d 2H, J=8.8 Hz)

HRMS (ESI$^-$): m/z Found 535.2380, calculated 535.2332 for [M+H]$^-$ (4.8 mmu)

(f) 2-COOH DFTM tert-Butyl 2-bromobenzoate (51 mg, 0.20 mmol) and anhydrous THF (3 mL) were put into a dried flask inside of which was substituted with argon. The mixture was cooled to −78° C., and then added with 1 M sec-BuLi (0.30 mmol), and the mixture was stirred for 20 minutes. The mixture was slowly added with 4,5-difluoro-3,6-diOTBDMS-Si-xanthone (5.4 mg, 0.010 mmol) dissolved in anhydrous THF (3 mL) at the same temperature, and the mixture was returned to room temperature. The mixture was stirred at room temperature for 1 hour, and then added with 2 N hydrochloric acid (10 mL), and the mixture was stirred for 20 minutes. The mixture was extracted with dichloromethane, and the organic layer was washed with brine, and dried over sodium sulfate. The solvent was removed, then the residue was added with TFA (3 mL), and the mixture was stirred at room temperature for 2 hours. The solvent was removed, and then the residue was purified by HPLC to obtain 2-COOH DFTM (2.2 mg, 0.054 mmol, yield 54%).

$^1$H-NMR (300 MHz, CD$_3$OD): δ 0.68 (s, 3H), 0.79 (s, 3H), 6.66 (d, 2H J=8.8 Hz), 6.87 (t, 2H, J=9.2 Hz), 7.13 (d, 1H J=7.3 Hz), 7.57-7.68 (m, 2H), 7.92 (d, 1H, J=8.1 Hz)

HRMS (ESI$^+$): m/z Found 411.0902, calculated 411.0864 for [M+H]$^+$ (3.8 mmu)

The optical characteristics of 2-COOH TM, 2-COOH DCTM, and 2-COOH DFTM obtained are shown in Table 1 mentioned below. The optical characteristics of 2-Me DCTM and 2-Me DFTM, which correspond to 2-COOH DCTM and 2-COOH DFTM in which the carboxy group is changed to methyl group, respectively, are also shown for reference. The measurement was performed in a 0.1 M phosphate buffer (pH 9) containing 1% dimethyl sulfoxide (DMSO). pKa was obtained from the absorbance meaured in a phosphate buffer (pH 9) by single-phase or two-phase curve fitting. The quantum yield was obtained by using the quantum yield (0.42) of 2-Me TokyoMagenta (2-Me TM, compound given in International Patent Publication WO2012/099218) in a 0.1 M phosphate buffer (pH 9) as the standard.

TABLE 1

| Compound | $\lambda_{max,abs}$ (nm) pH 3 | $\lambda_{max,abs}$ (nm) pH 9 | $\lambda_{max,fl}$ (nm) | pKa | $\Phi_{fl}$ |
|---|---|---|---|---|---|
| 2-Me TM | 472 | 582 | 598 | 6.8 | 0.42 |
| 2-Me DCTM | 477 | 595 | 607 | 5.2 | 0.48 |
| 2-Me DFTM | 465 | 583 | 598 | 5.3 | 0.57 |
| 2-COOH TM | | 582 | 598 | 8.3, 7.6 | 0.38 |
| 2-COOH DCTM | | 591 | 607 | 7.1, 7.0 | 0.48 |
| 2-COOH DFTM | | 581 | 596 | 7.1, 6.9 | 0.54 |

Example 6

Fluorescent Probe for Measurement of β-galactosidase

[Formula 7]

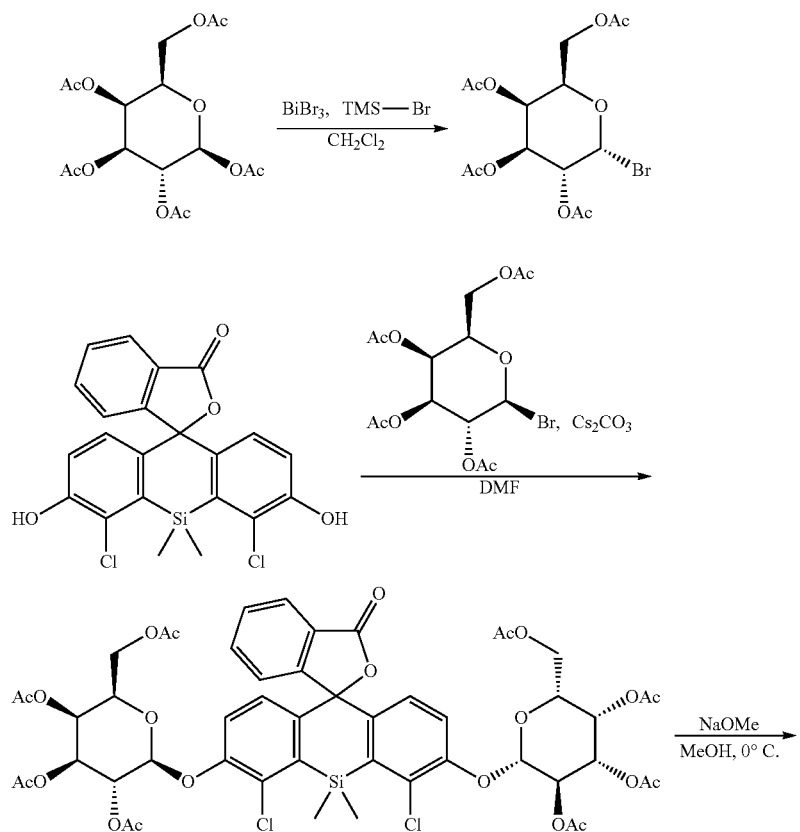

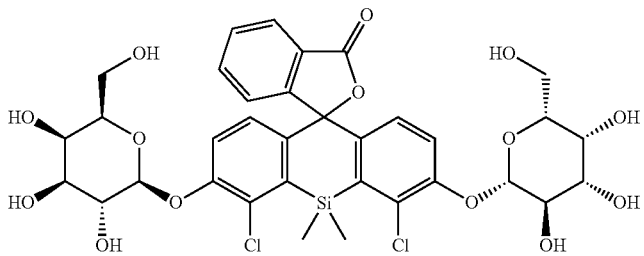

(a) 2,3,4,6-Tetra-O-acetyl-α-D-galactopyranosyl bromide

β-D-Galactose pentaacetate (5.00 g, 12.8 mmol) and bismuth(III) bromide (287 mg, 640 μmol) were dissolved in dichloromethane (25 mL), the solution was added with bromotriethylsilane (6.76 mL, 51.2 mmol), and the mixture was stirred at room temperature for 3 hours under an argon atmosphere. The reaction mixture was poured into aqueous saturated sodium hydrogencarbonate cooled on ice, then the mixture was extracted with dichloromethane, and the organic layer was washed with brine. The organic layer was dried over sodium sulfate, and the solvent was removed to obtain 2,3,4,6-tetra-O-acetyl-α-D-galactopyranosyl bromide (5.30 g, quantitative).

$^1$H NMR (300 MHz, CDCl$_3$): δ 2.01 (s, 3H), 2.06 (s, 3H), 2.12 (s, 3H), 2.15 (s, 3H), 4.08-4.22 (m, 2H), 4.47-4.51 (m, 1H), 5.05 (dd, 1H, J=3.8, 10.6 Hz), 5.41 (dd, 1H, J=3.3, 10.6 Hz), 5.51-5.52 (m, 1H), 6.70 (d, 1H, J=3.8 Hz)

$^{13}$C NMR (75 MHz, CDCl$_3$): δ 20.5, 20.5, 20.6, 20.7, 60.8, 66.9, 67.7, 68.0, 71.0, 88.1, 169.7, 169.8, 170.0, 170.3

(b) 4',5'-Dichloro-2-COOH TokyoMagenta di-(2',3',4',6'-tetra-O-acetyl-β-D-galactopyranoside)

45',5'-Dichloro-2-COOH TokyoMagenta (15.0 mg, 33.8 μmol) and cesium carbonate (Cs$_2$CO$_3$, 300 mg, 921 μmol) were dissolved in dimethylformamide (DMF, 1 mL), the solution was added with 2,3,4,6-tetra-O-acetyl-α-D-galactopyranosyl bromide (300 mg, 730 μmol) dissolved in DMF (1 mL), and the mixture was stirred overnight at room temperature under an argon atmosphere. After the insoluble matter was removed by filtration, and the solvent of the filtrate was removed, the residue was purified by HPLC to obtain 4',5'-dichloro-2-COOH TokyoMagenta di-(2',3',4',6'-tetra-O-acetyl-β-D-galactopyranoside) (16.2 mg, yield 43%).

$^1$H NMR (300 MHz, CD$_3$OD): δ 0.82 (s, 3H), 1.02 (s, 3H), 1.88 (s, 3H), 1.95 (s, 3H), 1.96 (s, 3H), 1.97 (s, 3H), 2,07 (s, 3H), 2.16 (s, 3H), 2.18 (s, 3H), 4.12-4.18 (m, 4H), 4.23-4.30 (m, 2H), 5.19-5.32 (m, 4H), 5.40-5.46 (m, 4H), 6.99 (d, 1H, J=7.3 Hz), 7.08-7.13 (m, 2H), 7.23-7.30 (m,2H), 7.52 (dd, 1H, J=6.6 Hz, 7.3 Hz), 7.61 (dd, 1H, J=6.6 Hz, 7.3 Hz), 7.95 (d, 1H, J=7.3 Hz)

$^{13}$C NMR (75 MHz, CD$_3$OD): δ 0.3, 0.5, 20.5, 20.5, 20.8, 62.4, 62.5, 68.6, 69.8, 72.0, 72.4, 90.3, 100.4, 100.8, 120.3, 120.8, 123.7, 123.7, 127.0, 127.6, 130.6, 130.8, 131.0, 136.0, 136.2, 136.7, 140.1, 140.4, 1.53.4, 153.6, 158.3, 171.2, 171.4, 171.4, 171.9, 171.9, 171.9, 172.5

HRMS (ESI$^+$); Calcd for [M+H]$^+$, 1103.21748; Found, 1103.21412 (−3.36 mmu).

(c) 4',5'-Dichloro-2-COOH TokyoMagenta di-β-D-galactopyranoside

4',5'-Dichloro-2-COOH TokyoMagenta Di-(2',3',4',6'-tetra-O-acetyl-β-D-galactopyranoside) (10.0 mg, 9.06 μmol) was dissolved in methanol (2 mL), and the solution was added with a 28% solution of NaOMe in methanol (6 μL) at 0° C. The mixture was stirred at 0° C. for 2 hours, and then neutralized by addition of Amberlite IR-120 plus (H$^+$). The Amberlite was removed by filtration, the solvent of the filtrate was removed, and then the residue was purified by HPLC to obtain 4',5'-dichloro-2-COOH TokyoMagenta diβ-D-galactopyranoside (diCl2-COOH-TM-diβGal, 6.65 mg, yield 96%).

$^1$H NMR (400 MHz, CD$_3$OD): δ 0.83 (s, 3H), 1.00 (s, 3H), 3.52-3.59 (m, 2H), 3.65-3.75 (m, 6H), 3.85-3.89 (m, 4H), 4.90 (d, 1H, J=7.7 Hz), 4.98 (d, 1H, J=7.7Hz), 6.98 (d, 1H, J=7.7 Hz), 7.04-7.07 (m, 2H), 7.26-7.30 (m, 2H), 7.51 (dd, 1H, J=6.8 Hz, 7.7 Hz), 7.59 (dd, 1H, J=6.8 Hz, 7.7 Hz), 7.91 (d, 1H, J=7.7 Hz)

$^{13}$C NMR (100 MHz, CD$_3$OD): δ −0.1, 0.6, 62.4, 70.2, 72.0, 72.0, 74.9, 77.2, 90.8, 102.2, 102.6, 119.4, 119.6, 123.7, 124.1, 126.9, 127.5, 127.6, 130.4, 130.4, 130.5, 136.0, 136.5, 138.8, 139.0, 154.0, 154.2, 158.5, 172.7

HRMS (ESI$^+$) Calcd for [M+Na]$^+$, 789.11491; Found, 789.11160 (−3.31 mmu)

(d) Evaluation of Function as Fluorescent Probe for Measurement of β-galactosidase

[Formula 8]

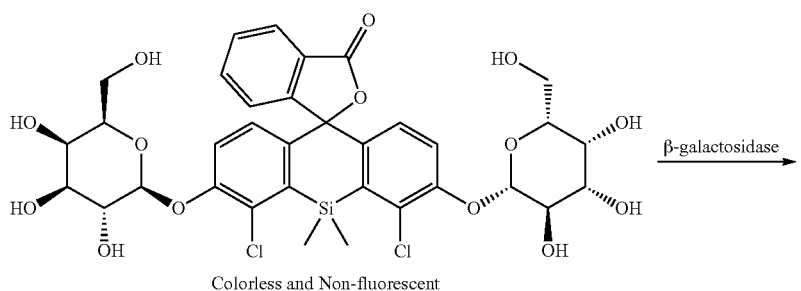

Colorless and Non-fluorescent

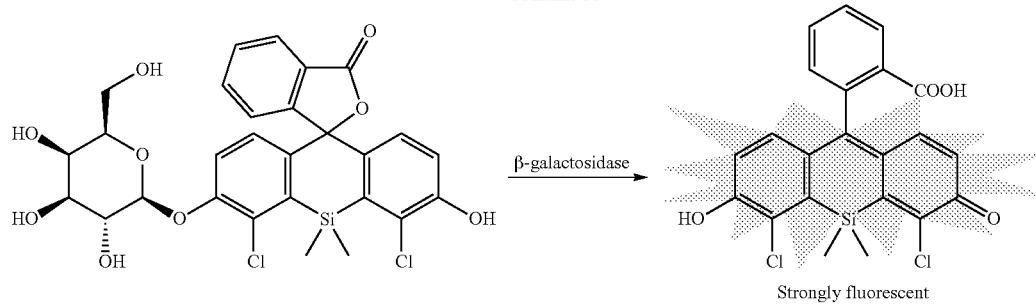

Figure 3:
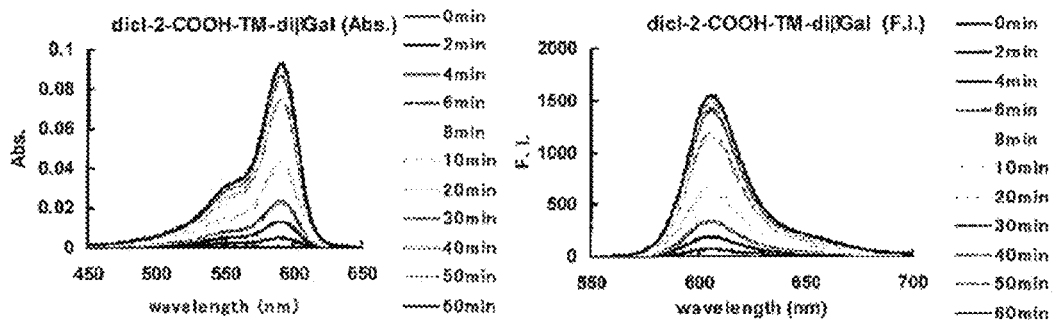
FIG. 3 shows results of observation of absorption spectra (left) and fluorescence spectra (right) over time performed during the reaction of diCl-2-COOH-TM-diβGal and β-galactosidase.
Figure 4:
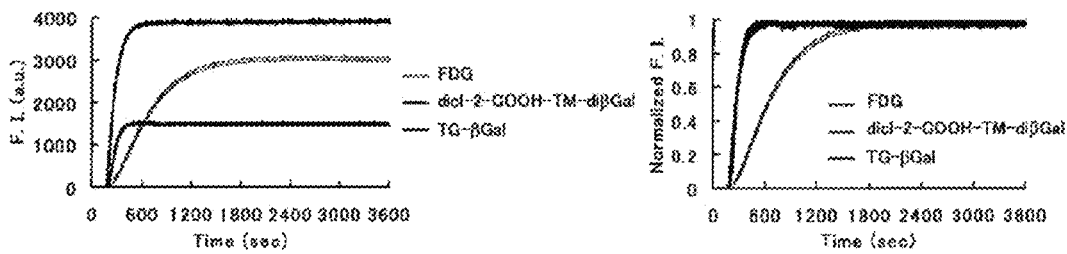
FIG. 4 shows results of measurement of fluorescence intensity change over time performed by adding diCl-2-COOH-TM-diβGal, FDG or TG-βGal, and β-galactosidase at the time point of 3 minutes. The left graph shows the results for measurement of fluorescence intensity over time, and the right graph shows normalized fluorescence intensity (blue, TG-βGal; red, diCl-2-COOH-TM-DiβGal; and green, FDG).

Function of the compound obtained in (c) mentioned above as a fluorescent probe for measurement of β-galactosidase activity was examined. The reaction scheme according to which the compound functions as a fluorescent probe for measurement of β-galactosidase activity is as described above, and both the β-galactose residues introduced as $R^8$ and $R^9$ are hydrolyzed to give a compound of the ring-open state, which emits strong red fluorescence.

diCl-2-COOH-TM-diβGal (1 μM) and β-galactosidase (0.15 unit) were reacted, and the absorption spectrum and the fluorescence spectrum were observed over time. The results are shown in FIG. 3. The reaction was performed at 37° C. in a 0.1 M sodium phosphate buffer (pH 7.4, 3 mL) containing 1 mM magnesium chloride ($MgCl_2$), 14.3 mM 2-mercaptoethanol, and 0.1% dimethyl sulfoxide (DMSO). The excitation wavelength for fluorescence was 591 nm. Further, a 0.1 M sodium. phosphate buffer (pH 7.4, 3 mL) containing 1 mM $MgCl_2$, 14.3 mM 2-mercaptoethanol, and 0.1% DMSO was added with diCl-2-COOH-TM-diβGal (1 μM), FDG P(1 μM) or TG-βGal (1 μM), and β-galactosidase (1.5 units) at the time point of 3 minutes, and change of fluorescence intensity was measured over time. The results are shown in FIG. 4. The left graph shows the results for measurement of fluorescence intensity over time, and the right graph shows normalized fluorescence intensity (blue, TG-βGal; red, diCl-2-COOH-TM-DiβGal; and green, FDG). The excitation wavelength and the fluorescence wavelength were 491 nm and 509 nm, respectively, for FDG and TG-βGal, and the excitation wavelength and the fluorescence wavelength were 591 nm and 607 nm, respectively, for diCl-2-COOH-TM-diβGal.

(e) Inhibition Effect of β-galactosidase Inhibitor

Figure 5:
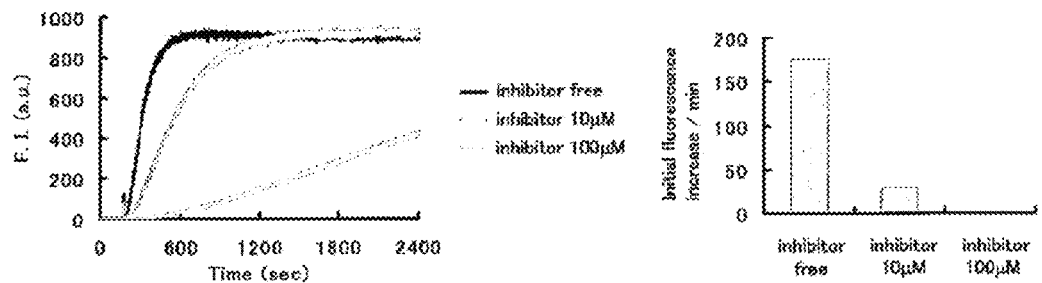
FIG. 5 shows results of observation of fluorescence intensity over time performed during the reaction of diCl-2-COOH-TM-diβGal, β-galactosidase, and β-galactosylamidine as a β-galactosidase inhibitor at 37° C. The left graph shows changes of fluorescence intensity over time, and the right graph shows increase of fluorescence at an early stage of the observation.

A 0.1 M sodium phosphate buffer (pH 7.4, 500 μL) containing 1 mM $MgCl_2$, 14.3 mM 2-mercaptoethanol, and 1.1% DMSO was added with diCl-2-COOH-TM-diβGal (1 μM), β-galactosidase (0.5 unit), and β-galactosylamidine (10 μM or 100 μM) as a β-galactosidase inhibitor at the time point of 3 minutes, the reaction was allowed at 37° C., and the fluorescence spectrum was observed over time. The results are shown in FIG. 5. The excitation wavelength was 591 nm, and the fluorescence wavelength was 607 nm.

Example 7

Fluorescent Probe for Measurement of β-galactosidase

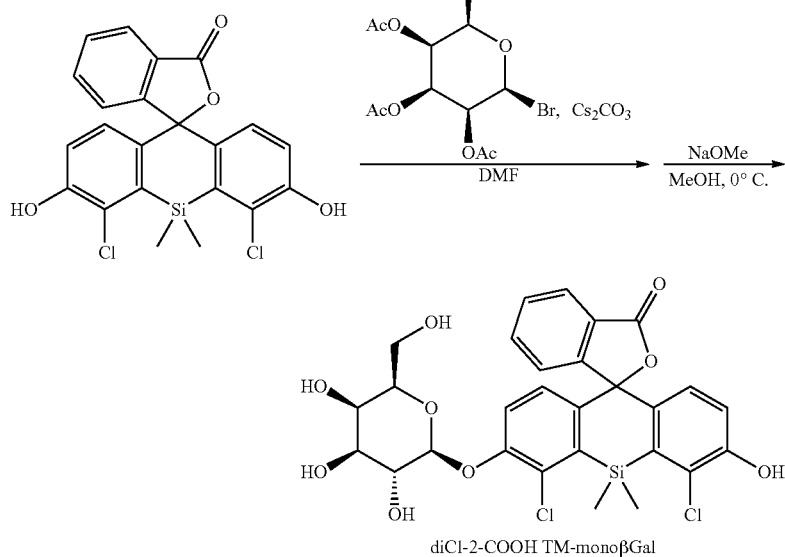

diCl-2-COOH TM-monoβGal (a) 4',5'-Dichloro-2-COOH TokyoMagenta mono-β-D-galactopyranoside (diCl-2-COOH TM-monoβGal)

4',5'-Dichloro-2-COOH TokyoMagenta (15.0 mg, 33.8 μmol) and $Cs_2CO_3$ (17.0 mg, 52.1 μmol) were dissolved in DMF (1 mL), the solution was added with 2,3,4,6-tetra-O-acetyl-α-D-galactopyranosyl bromide (20 mg, 48.6 μmol) dissolved in DMF (1 mL), and the mixture was stirred overnight at room temperature under an argon atmosphere. The insoluble matter was removed by filtration, the solvent of the filtrate was removed, and then the residue was purified by HPLC. The purified product was dissolved in methanol (3 mL), and the solution was added with a 28% solution of sodium methoxide in methanol (6 μL) at 0° C. The mixture was stirred at 0° C. for 2 hours, and then neutralized by addition of Amberlite IR-120 plus ($H^+$). The Amberlite was removed by filtration, the solvent of the filtrate was removed, and then the residue was purified by HPLC to obtain 4',5'-dichloro-2-COOH TokyoMagenta mono-β-D-galactopyranoside (4.09 mg, yield 20%). The product was analyzed by HPLC with a detection wavelength of 250 nm. As a result, a single peak was observed at 12.0 minutes (eluent A (water, 0.1 M TEAA (tetraethylammonium acetate) and eluent B (80% acetonitrile/$H_2O$, 0.1M TEAA), gradient A:B=80:20 to 0:100 (15 minutes)).

$^{H\text{-}NMR}$ (400 MHz, $CD_3OD$): 0.83 (s, 3H), 0.99 (s, 3H), 3.52-3.58 (m, 1H), 3.67-3.75 (m, 3H), 3.85-3.89 (m, 2H), 4.89-4.98 (m, 1H), 6.89 (m, 2H), 6.97-7.03 (m, 2H), 7.25-7.29 (m, 1H), 7.51 (dd, 1H, J=7.2 Hz, 8.0 Hz), 7.59 (dd, 1H, J=7.2, 8.0 Hz), 7.91 (d, 1H, J=7.2 Hz)

HRMS ($ESI^+$): Calcd for $[M+Na]^+$, 627.0621; Found, 627.0669 (+4.8 mmu)

The optical characteristics of diCl-2-COOH TM-monoβ-Gal obtained are shown in Table 2 mentioned below. The measurement was performed in a 0.1 M phosphate buffer. The quantum yield was calculated by using the quantum yield (0.85) of fluorescein in 0.1M aqueous sodium hydroxide as the standard.

TABLE 2

| | Absorption $\lambda_{max}$ [nm] | Fluorescence $\lambda_{max}$ [nm] | Quantum yield $\Phi_{fl}$ | Extinction Coefficient ε [$M^{-1}cm^{-1}$] |
|---|---|---|---|---|
| diCl-2-COOH TM-monoβGal | 460 | 555 | 0.09 (pH 7.4) | 1,200 (pH 7.4) |

Figure 6:
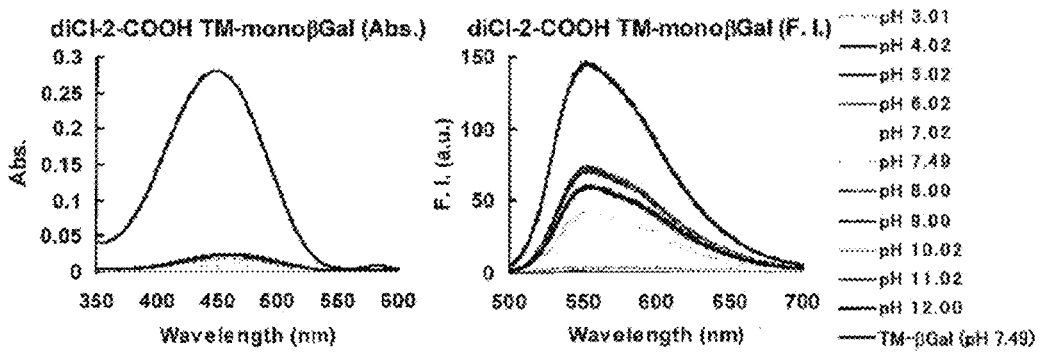
FIG. 6 shows results of comparison with TM-βGal, which always exists with the open-ring structure, which was performed for estimating open-ring rate of diCl-2-COOH TM-monoβGal.

In order to estimate the open-ring ratio of diCl-2-COOH TM-monoβGal, comparison with the absorption spectrum of TM-βGal was performed. Since TM-βGal always exists as the open-ring structure without being influenced by pH, the absorption spectrum thereof does not change in accordance with pH change. Compared with such TM-βGal, the value of the absorbance of diCl-2-COOH TM-monoβGal was smaller under pH of physiological conditions, and most part thereof (more than 95%) had the ring-closed structure, which does not show absorption (FIG. 6). The measurement was performed by using 10 μM diCl-2-COOH TM-monoβGal in a 0.1 M sodium phosphate buffer of various pH values containing 1.0% DMSO. The excitation wavelength was 450 nm for TMβGal (compound described in International Patent Publication WO2012/099218), or 460 nm for diCl-2-COOH TM-monoβGal.

[Formula 10]

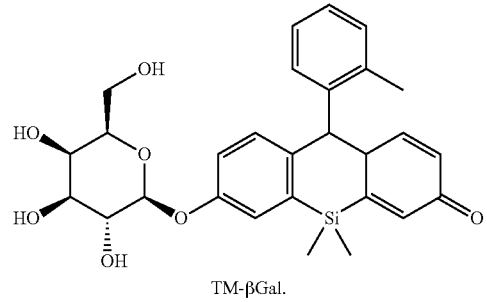

TM-βGal.

(b) Evaluation of Function as Fluorescent Probe for Measurement of β-galactosidase Activity Function of diCl-2-COOH TM-monoβGal as a fluorescent probe for measurement of the β-galactosidase activity was examined. The reaction scheme according to which this compound functions as a fluorescent probe for measurement of the β-galactosidase activity is as described below, and the β-galactose residue introduced as $R^8$ is hydrolyzed to give a compound wherein $R^8$ and $R^9$ are hydrogen atoms, which changes into a compound of the open-ring state, and thus comes to emit strong red fluorescence.

[Formula 11]

Figure 7:
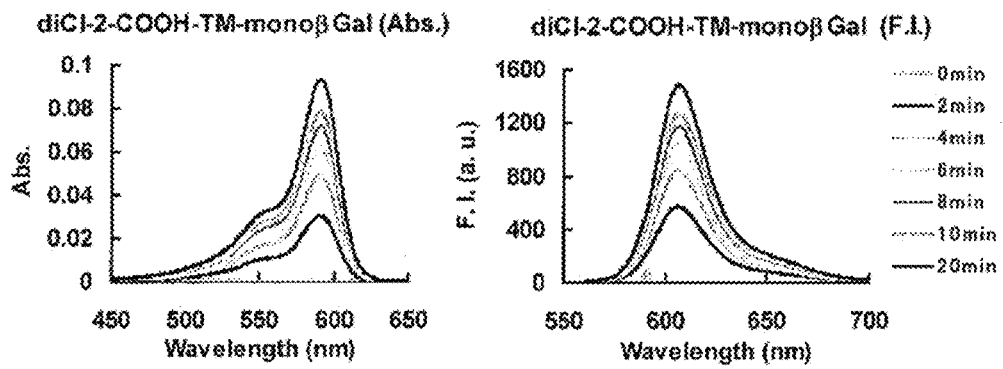
FIG.7 shows results of observation of absorption spectra (left) and fluorescence spectra (right) over time performed during the reaction of diCl-2-COOH-TM-monoβGal and β-galactosidase.

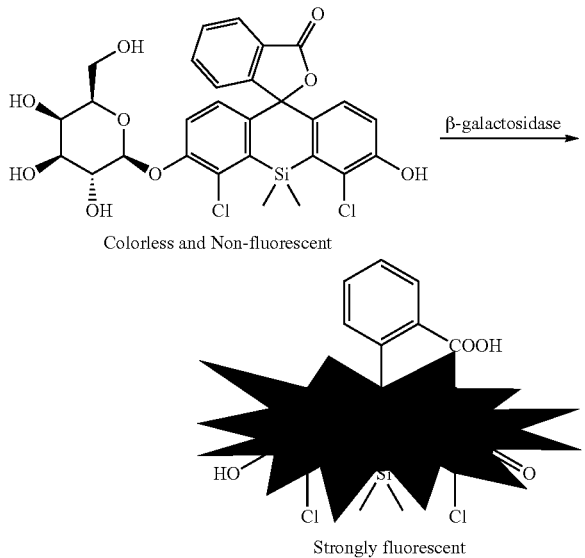

diCl-2-COOH-TM-monoβGal (1 μM) and β-galactosidase (0.3 unit) were reacted, and the absorption spectrum and the fluorescence spectrum were observed over time. The results are shown in FIG. 7. The reaction was performed at 37° C. in a 0.1 M sodium phosphate buffer (pH 7.4, 3 mL) containing 1 mM $MgCl_2$, 14.3 mM 2-mercaptoethanol, and 0.1% DMSO. The fluorescence spectrum was measured with an excitation wavelength of 591 nm.

Figure 8:
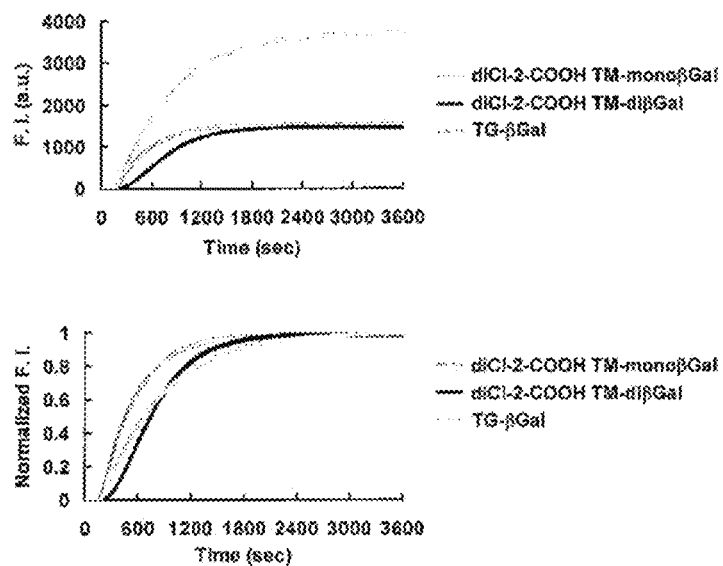
FIG. 8 shows results of measurement of fluorescence intensity change over time performed by adding diCl-2-COOH-TM-diβGal (1 μM), diCl-2-COOH-TM-monoβGal (1 μM) or TG-βGal (1 μM), and β-galactosidase (1.5 units).

Further, a 0.1 M sodium phosphate buffer (pH 7.4, 3 mL) containing 1 mM $MgCl_2$, 14.3 mM 2-mercaptoethanol, and 0.1% DMSO was added with diCl-2-COOH-TM-di βGal (1 μM), diCl-2-COOH-TM-monoβGal (1 μM) or TG-μGal (1 μM), and β-galactosidase (1.5 units) at the time point of 3 minutes, and change of fluorescence intensity was measured over time. The results, are shown in FIG. 8. The upper graph shows the fluorescence intensity observed over time, and the lower graph shows normalized fluorescence intensity. The excitation wavelength and the fluorescence wavelength were 491 nm and 509 nm, respectively, for TG-βGal, and the excitation wavelength and the fluorescence wavelength were 591 nm and 607 nm, respectively, for diCl-2-COOH-TM-diβGal and diCl-2-COOH-TM-monoβGal.

Figure 9:
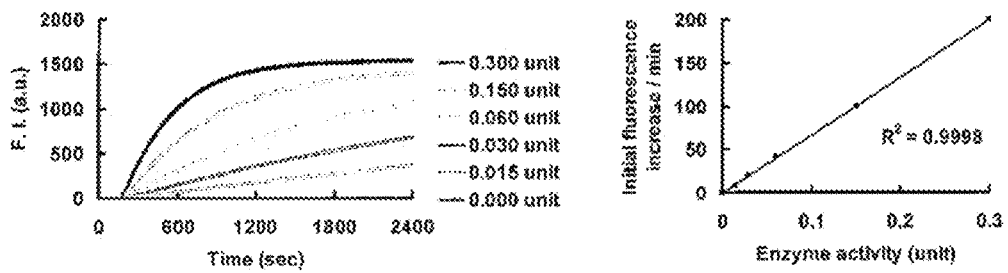
FIG. 9 shows results of examination of enzyme concentration dependency of the enzyme-substrate reaction of diCl-2-COOH-TM-monoβGal and β-galactosidase. The left graph shows fluorescence intensity observed over time at each enzyme concentration, and the right graph shows correlation of the amount of added β-galactosidase and increase of fluorescence.

Enzyme concentration dependency of the enzyme-substrate reaction of diCl-2-COOH-TM-monoβGal and β-galactosidase was examined. A 0.1 M sodium phosphate buffer (pH 7.4, 3 mL) containing 1 mM $MgCl_2$, 14.3 mM 2-mercaptoethanol, and 0.1% DMSO was added with diCl-2-COOH-TM-monoβGal (1 μM), and added with β-galactosidase at various concentrations 3 minutes afterward. The measurement was performed with an excitation wavelength of 591 nm and a fluorescence wavelength of 607 nm. The results are shown in FIG. 9. The right graph shows correlation of the amount of added β-galactosidase and increase of fluorescence.

(c) Inhibition Effect of β-galactosidase Inhibitor

Figure 10:
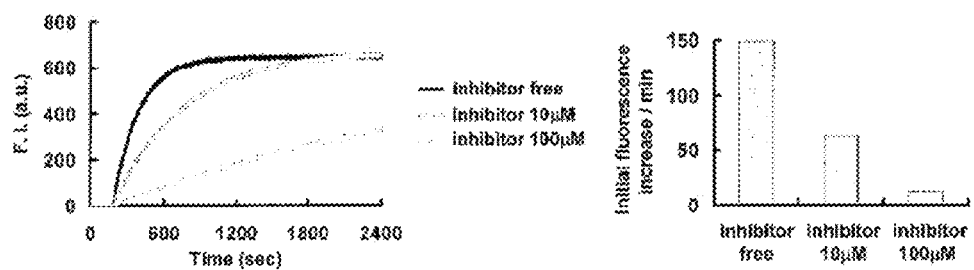
FIG. 10 shows results of observation of fluorescence intensity performed over time performed during the reaction of diCl-2-COOH-TM-monoβGal (1 μM), β-galactosidase (0.09 unit) and β-galactosylamidine (10 μM or 100 μM) as a β-galactosidase inhibitor at 37° C. The left graph shows fluorescence intensity observed over time, and the right graph shows increase of fluorescence at an early stage of the observation.

A 0.1 M sodium phosphate buffer (pH 7.4, 500 μL) containing 1 mM $MgCl_2$, 14.3 mM 2-mercaptoethanol, and 2.0% DMSO was added with diCl-2-COOH-TM-monoβGal (1 μM), β-galactosidase (0.09 unit), and β-galactosylamidine (10 μM or 100 μM) as β-galactosidase inhibitor at the time point of 3 minutes the reaction was allowed at 37° C., and the fluorescence spectrum was observed over time. The results are shown in FIG. 10. The excitation wavelength was 591 nm, and the fluorescence wavelength was 607 nm Example 8

Fluorescent Probe for Measurement of Esterase (a) 3',6', Bis(acetyloxy)-4',5'-dichloro-2-COOH TokyoMagenta (diCl-2-COOH TM-diacetyl)

[Formula 12]

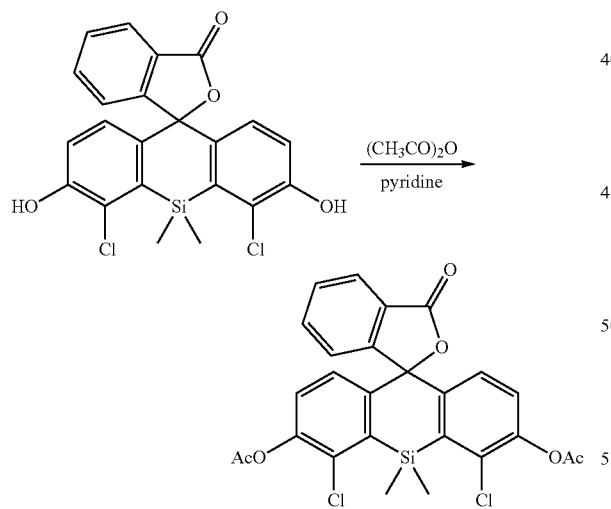

4',5'-Dichloro-2-COOH TokyoMagenta (15.0 mg, 33.8 μmol) was dissolved in pyridine (1.5 mL), the solution was added with acetic anhydride (100 μL), and the mixture was stirred at room temperature for 1 hour under an argon atmosphere. After the solvent was removed, the residue was purified by HPLC to obtain 4',5'-dichloro-2-COOH TokyoMagenta diacetyl (10.4 mg, yield 58%).

$^1$H NMR (300 MHz, $CD_3OD$): δ 0.85 (s, 3H), 1.05 (s, 3H), 2.33 (s, 6H), 7.05 (d, 1H, J=7.8 Hz), 7.20 (d, 2H, J=8.8 Hz), 7.25 (d, 2H, J=8.8 Hz), 7.67 (dd 1H, J=1.2, 7.6, 7.8Hz), 7.80 (ddd, 1H, J=1.5, 7.6, 8.1 Hz), 7.90 (d, 1H, J=8.1 Hz)

$^{13}$C NMR (75 MHz, $CD_3OD$): δ 0.6, 0.2, 20.7, 88.8, 122.4, 122.7, 125.6, 126.1, 126.2, 129.2, 133.2, 134.8, 135.3, 142.4, 146.8, 156.4, 168.2, 170.9

HRMS (ESI$^+$): Cald for [M+H]$^+$, 527.04844 Found, 527.04928 (+0.83 mmu)

(b) Fluorescent Probe for Measurement of Esterase

Function of the compound obtained above as a fluorescent probe for measurement of esterase was examined. The reaction scheme according to which the compound functions as a substrate of esterase is a described above, and both the acetyl groups introduced as $R^8$ and $R^9$ are hydrolyzed to give a compound of the ring-open state, which emits strong red fluorescence.

[Formula 13]

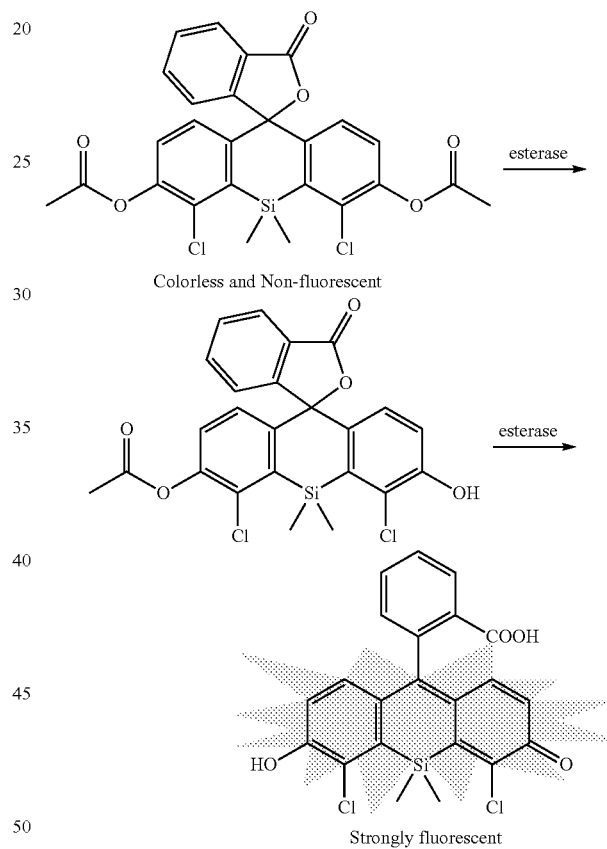

Figure 11:
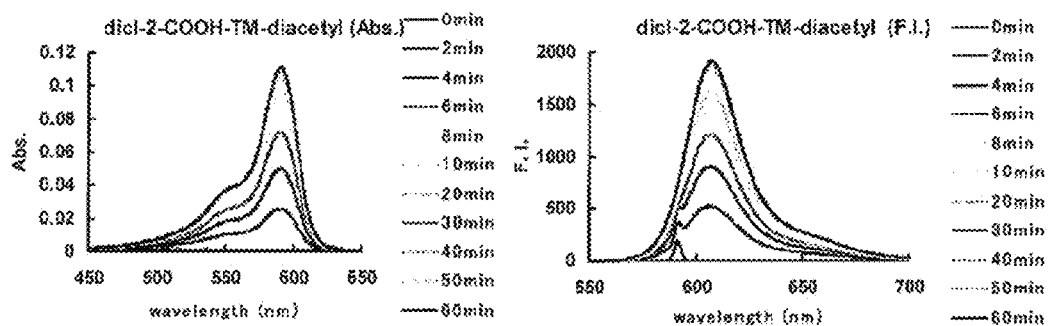
FIG. 11 shows results obtained by reacting diCl-2-COOH TM-diacetyl and PLE (pig liver esterase). The left graph shows changes of fluorescence intensity over time, and the right graph shows change of fluorescence spectra over time.
Figure 12:
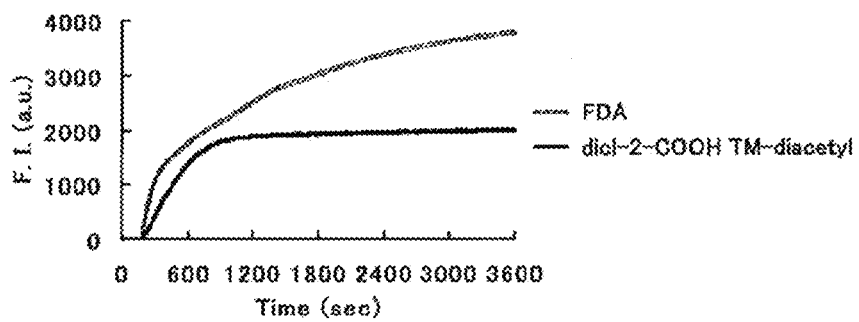
FIG. 12 shows results of measurement of fluorescence intensity change over time performed during the reaction of diCl-2-COOH TM-diacetyl and PLE in vitro.

The enzyme-substrate reaction of diCl-2-COOH TM-diacetyl and PLE (pig liver esterase) was examined. A 0.1 M sodium phosphate buffer (pH 7.4, 3 mL) containing 0.1% DMSO was added with diCl-2-COOH TM-diacetyl (1 μM) and PLE (0.1 unit), and the reaction was allowed at 37° C. The excitation wavelength was 591 nm, Changes of the absorption and fluorescence over time are shown in FIG. 11. Further, change of fluorescence intensity was measured over time in an in vitro reaction of diCl-2-COOH TM-diacetyl, FDA (fluorescein diacetate, CAS [596-09-8]), and PLE. The results are of shown in FIG. 12 (FDA, green; diCl-2-COOH TM-diacetyl, red). The reaction was performed at 37° C. by adding diCl-2-COOH TM-diacetyl (1 μM) or FDA (1 μM) and PLE of (0.1 unit) to a 0.1 M sodium phosphate buffer (pH 7.4, 3 mL) containing 0.1% DMSO at the time point of 3 minutes. The excitation wavelength and the fluorescence wavelength were 491 nm and 509 nm, respectively, for FDA, and the excitation wavelength and the fluorescence wavelength were 591 nm and 607 nm, respectively, for diCl-2-COOH TM-diacetyl.

Figure 13:
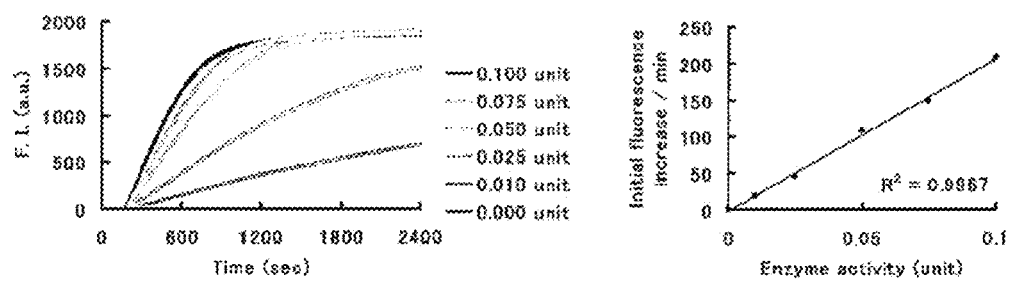
FIG. 13 shows results of examination on enzyme concentration dependency of the enzyme-substrate reaction of diCl-2-COOH TM-diacetyl and PLE. The left graph shows fluorescence intensity observed over time at each enzyme concentration, and the right graph shows correlation of the amount of added PLE and increase of fluorescence.

Enzyme concentration dependency of the enzyme-substrate reaction of diCl-2-COOH TM-diacetyl and PLE was examined. A 0.1 M sodium phosphate buffer (pH 7.4, 3 mL) containing 0.1% DMSO was added with diCl-2-COOH TM-diacetyl (1 μM) or FDA (1 μM), and PLE of various concentrations at the time point of 3 minutes, and the reaction was allowed at 37° C. Change of fluorescence was measured over time with an excitation wavelength of 591 nm and a fluorescence wavelength of 607 nm. The results are shown in FIG. 13.

(c) Inhibition Effect of Esterase Inhibitor

Figure 14:
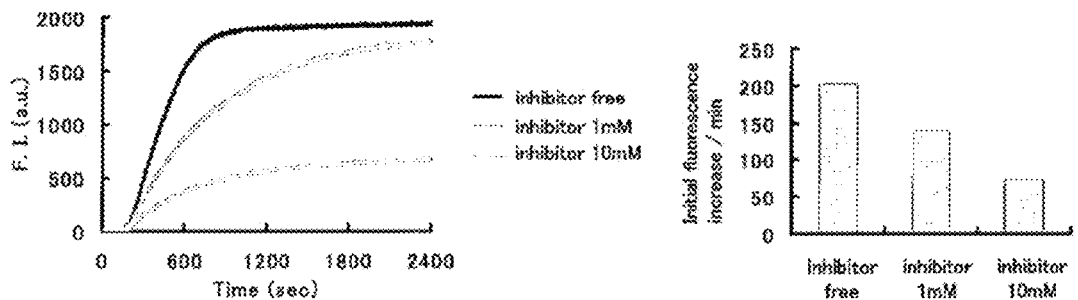
FIG. 14 shows results of observation of fluorescence intensity over time performed during the reaction of diCl-2-COOH-TM-diacetyl, PLE and AEBSF as an esterase inhibitor at 37° C. The left graph shows fluorescence intensity observed over time, and the right graph shows increase of fluorescence at an early stage of the observation.

A 0.1 M sodium phosphate buffer (pH 7.4, 3 mL) containing 1.1% DMSO was added with diCl-2-COOH TM-diacetyl (1 μM), PLE (0.1 unit), and AEBSF (1 mM or 10 mM) as an esterase inhibitor at the time point of 3 minutes, and the reaction was allowed at 37° C. Change of the fluorescence was observed over time with an excitation wavelength of 591 nm, and a fluorescence wavelength of 607 nm. The results are shown in FIG. 14.

Example 9

Fluorescent Probe for Staining Live Cells (a) diCl-Si-half-calcein AM

A compound corresponding to the probe for measurement of esterase obtained in Example 8 introduced with N,N'-bis(acetoxymethyloxycarbonylmethyl)aminomethyl group as a hydrophilic substituent was prepared according to the following scheme.

[Formula 14]

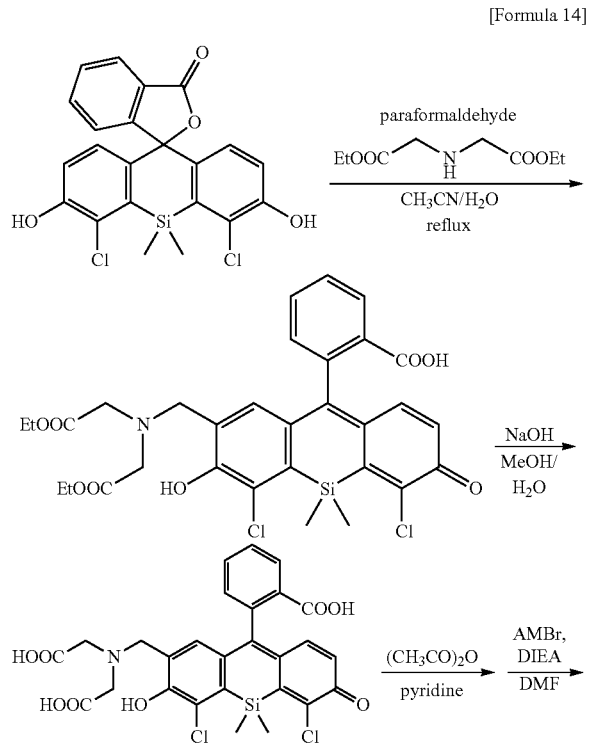

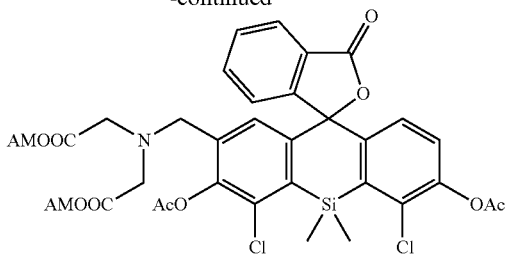

(a) 4',5'-Dichloro-7'-[N,N'-bis(carboxymethyl)aminomethyl]-2-COOH TokyoMagenta diethyl ester 4',5'-Dichloro-2-COOH TokyoMagenta (40.0 mg, 90.2 μmol), diethyl iminodiacetate (200 μL), and paraformaldehyde (400 mg) were suspended in a mixed solvent of acetonitrile (5.25 mL) and water (2.25 mL), and the suspension was refluxed by heating for two days under an argon atmosphere. The residue was purified by HPLC to obtain 4',5'-dichloro-7'-[N,N'-bis(carboxymethyl)aminomethyl]-2-COOH TokyoMagenta diethyl ester (20.2 mg, yield 35%).

$^1$H NMR (300 MHz, CD$_3$OD) δ 0.83 (s, 3H), 0.98 (s, 3H), 1.22 (t, 6H, J=7.2 Hz), 3.41 (s, 4H), 3.80 (s, 2H), 4.10-4.14 (m, 4H), 6.69 (s, 1H), 6.85-6.87 (m, 2H), 6.98 (d, 1H, J=7.5 Hz), 7.49 (dd, 1H, J=7.5, 8.1 Hz), 7.58 (dd, 1H, J=7.5, 8.1 Hz), 7.89 (d, 1H, J=7.5 Hz)

$^{13}$C NMR (75 MHz, CD$_3$OD): δ −0.1, 0.5, 14.5, 55.0, 56.5, 62.1, 91.2, 119.6, 123.8, 124.3, 126.7, 127.1, 127.8, 127.9, 128.1, 130.2, 135.5, 135.7, 135.9, 136.3, 186.5, 153.9, 154.3, 158.7, 172.4, 172.9

HRMS (ESI$^+$): Calcd for [M+H]$^+$, 644.12742 Found, 644.12867 (+1.24 mmu)

(b) 4',5'-Dichloro-7'-[N,N'-bis(carboxymethyl)aminomethyl]-2-COOH TokyoMagenta (diCl-Si-half-calcein)

4',5'-Dichloro-7'-[N,N'-bis(carboxymethyl)aminomethyl]-2-COOH TokyoMagenta diethyl ester (15.0 mg, 23.3 μmol) was dissolved in methanol (1.0 mL), the solution was added with 2 N NaOH (1.0 mL, 2.0 mmol), and the mixture was stirred at room temperature for 2 hours. After the methanol was removed, the residue was purified by HPLC to obtain 4',5'-dichloro-7'-[N,N'-bis (carboxymethyl)aminomethyl]-2-COOH TokyoMagenta (11.0 mg, yield 80%).

$^1$NMR (300 MHz, DMF-d$_7$): δ 0.82 (s, 3H), 1.00 (s, 3H), 3.20 (s, 4H), 3.74 (s, 2H), 6.74 (s, 1H), 6.92 (d, 1H, J=8.8 Hz), 7.10-7.13 (m, 2H), 7.56 (dd, 1H, J=7.2, 8.1 Hz), 7.68 (dd, 1H, J=7.2, 7.6 Hz), 7.90 (d, 1H, J=8.1 Hz)

$^{13}$C NMR (100 MHz, D$_2$+NaOD): δ −3.3, −3.0, 56.5, 57.4, 122.3, 125.4, 126.8, 129.0, 129.2, 129.9, 130.4, 136.7, 137.3, 139.1, 139.7, 142.3, 143.5, 143.8, 144.2, 171.1, 173.7, 173.8, 175.3

HRMS (ESI$^+$): Calcd for [M+Na]$^+$, 610.04677 Found, 610.04367 (−3.10 mmu)

(c) 3',6'-Bis(acetyloxy)4',5'-dichloro-7'-[N,N'-bis(carboxymethyl)aminomethyl]-2-COOH TokyoMagenta diacetoxymethyl ester (diCl-Si-half-calcein AM)

4',5'-Dichloro-7'-[N,N'-bis(carboxymethyl)aminomethyl]-2-COOH TokyoMagenta (8.0 mg, 13.6 μmol) was dissolved in pyridine (1.0 mL), the solution was added with acetic anhydride (30.0 μL, 317 μmol), and the mixture was stirred at room temperature for 3 hours. The solvent, was removed, and then the residue was dissolved in acetonitrile (1.0 mL). The solution was added four times with N-ethyldiisopropylamine (9.0 μL, 51.7 μmol) and bromomethyl acetate (5.1 μL, 46.1 μmol) every 3 hours under an argon atmosphere, and the mixture was stirred at room temperature. The resultant was purified by HPLC to obtain 3',6'-bis(acetyloxy)-4',5'- dichloro-7'-[N,N'-bis(carboxymethyl)aminomethyl]-2COOH TokyoMagenta diacetoxymethyl ester (1.8 mg, yield 16%).

¹H-NMR (300 MHz, CD₃CN): δ 0.72 (s, 3H), 0.94 (s, 3H), 1.95 (s, 6H), 2.21 (s, 3H), 2.23 (s, 3H), 3.27 (s, 4H), 3.57-3.71 (m, 2H), 5.55 (s, 4H), 6.94 (d, 1H, J=7.6 Hz), 7.11 (d, 1H, J=8.8 Hz), 7.14 (d, 1H, J=8.8 Hz), 7.28 (s, 1H), 7.43-7.48 (m, 1H), 7.51-7.55 (m, 1H), 7.64 (d, 1H J=7.3 Hz)

HRMS (ESI⁺): Calcd for [M+Na]⁺, 838.1102; Found, 838.1079 (−2.3 mmu)

In the HPLC analysis (detection at 250 nm), a single peak was observed at 13.2 minutes (eluent A (water, 0.1% acetic acid) and eluent B (80% acetonitrile/water, 0.1 M acetic acid), gradient A:B=80:20 to 0:100 (10 minutes)).

(d) The Enzyme-Substrate Reaction of diCl-Si-Half-Calcein AM and PLE was Examined.

Figure 15:
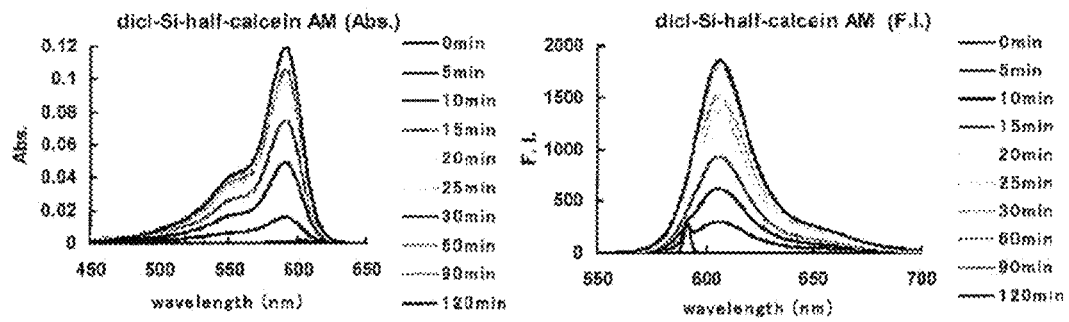
FIG. 15 shows results of measurement of fluorescence change over time performed during the reaction of diCl-Si-half-calcein AM and PLE. The left graph shows changes of absorption spectra over time, and the right graph shows change of fluorescence spectra over time.
Figure 16:
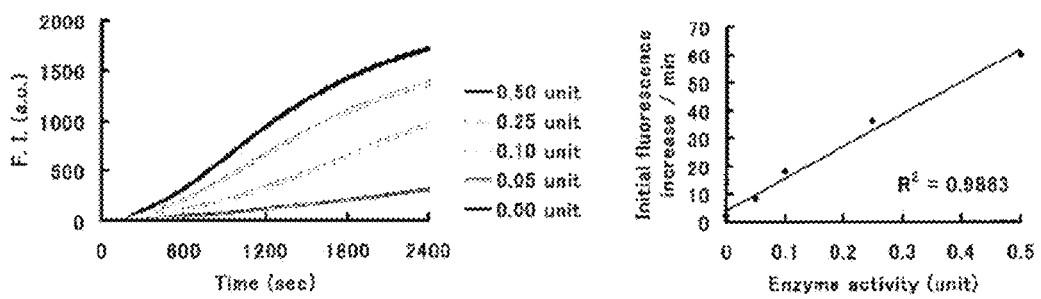
FIG. 16 shows results of examination on enzyme concentration dependency of the enzyme-substrate reaction of diCl-Si-half-calcein AM and PLE. The left graph shows fluorescence intensity change over time observed at each enzyme concentration, and the right graph shows correlation of the amount of added PLE and increase of fluorescence.

A 0.1 M sodium phosphate buffer (pH 7.4, 3 mL) containing 0.1% DMSO was added with diCl-Si-half-calcein AM (1 µM) and PLE (1.0 unit), and the reaction was allowed at 37° C. The excitation wavelength was 591 nm. Changes of the absorption and fluorescence over time are shown in FIG. 15. Further, enzyme concentration dependency of the enzyme-substrate reaction of diCl-Si-half-calcein AM and PLE was examined. A 0.1 M sodium phosphate buffer (pH 7.4, 3 mL) containing 0.1% DMSO was added with diCl-Si-half-calcein AM (1 µM) and PLE of various concentrations at the time point of 3 minutes, and the reaction was allowed at 37° C. Change of the fluorescence was measured over time with an excitation wavelength of 591 nm, and a fluorescence wavelength of 607 nm. The results are shown in FIG. 16.

(e) Inhibition Effect of Esterase Inhibitor

Figure 17:
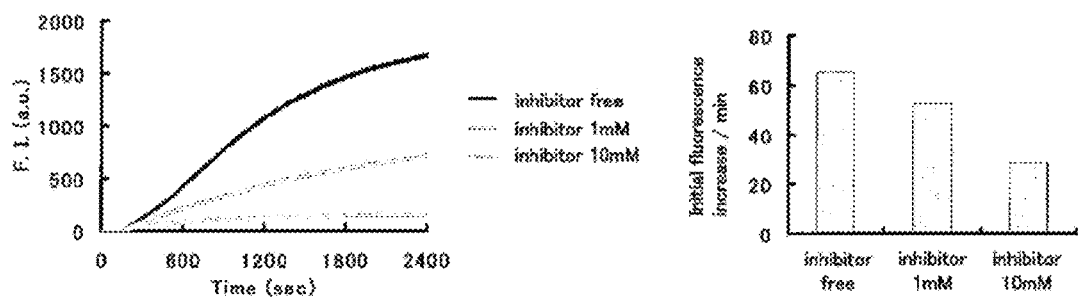
FIG. 17 shows results of observation of fluorescence intensity over time performed during the reaction of diCl-Si-half-calcein AM, PLE and AEBSF as an esterase inhibitor at 37° C. The left graph shows fluorescence intensity observed over time, and the right graph shows increase of fluorescence at an early stage of the observation.

A 0.1 M sodium phosphate buffer (pH 7.4, 3 mL) containing 1.1% DMSO was added with diCl-Si-half-calcein AM (1 µM) PLE (1.0 unit), and AEBSF (1 mM or 10 mM) as an esterase inhibitor at the time point of 3 minutes, and the reaction was allowed at 37° C. Change of the fluorescence was measured over time with an excitation wavelength of 591 nm, and a fluorescence wavelength of 607 nm. The results are shown in FIG. 17.

(f) The Esterase Activity in Live Cells was Imaged by Using diCl-Si-Half-Calcein AM.

Figure 18:
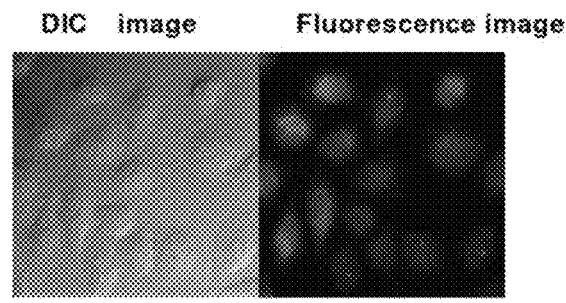
FIG. 18 shows result of imaging of the esterase activity in live cells performed by using diCl-Si-half-calcein AM.

The HeLa cells were incubated at 37° C. for 30 minutes with 3 µM diCl-Si-half-calcein AM in the Dulbecco's Modified Eagle's medium (DMEM) containing 0.3% dimethyl sulfoxide. The cells were washed twice with PBS, then the medium was replaced with HBSS (Hank's Balanced Salt Solution), and the cells were observed with an excitation wavelength of 565 to 585 nm and detection wavelength of 600 to 690 nm by using an incident light fluorescence microscope IX-71 (Olympus). The result is shown in FIG. 18.

Example 10

Figure 19:
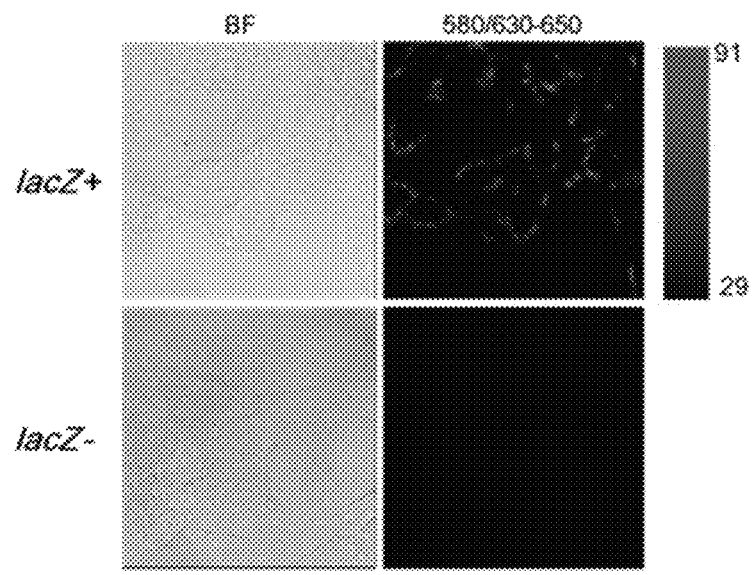
FIG. 19 shows result of imaging of the β-galactosidase activity in live cells performed by using diCl-2-COOH TM-monoβGal.
Figure 20:
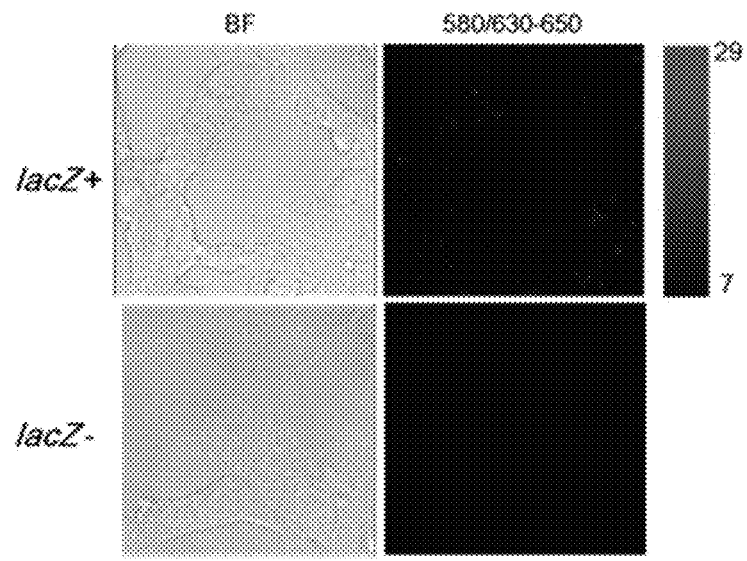
FIG. 20 shows result of imaging of the β-galactosidase activity in live cells performed by using diCl-2-COOH TM-diβGal.

For the HEK293 cells in which the lacZ gene encoding β-galactosidase was stably expressed (lacZ+), and the HEK293 cells into which the lacZ gene was not introduced (lacZ−) as a control, β-galactosidase in the cells was measured by using diCl-2-COOH TM-monoβGal or diCl-2-COOH TM-diβGal. The HEK293 cells (lacZ−) were incubated at 37° C. for 30 minutes in the Dulbecco's Modified Eagle's medium (DMEM) containing 0.1% DMSO together with 10 µM diCl-2-COOH TM-monoβGal or diCl-2-COOH TM-diβGal. The cells were observed with an excitation wavelength of 580 nm and fluorescence wavelength of 630 to 650 nm by using a confocal microscope SP5 (Leica). The results are shown in FIG. 19 (diCl-2-COOH TM-monoβGal) and FIG. 20 (diCl-2COOHTM-diβGal). The intracellular uptaking amount of the mono-substituted compound, diCl-2-COOH TM-monoβGal, was larger than that of highly water-soluble diCl-2-COOH TM-diβGal, and therefore suitability of the former for application to cells was demonstrated.

What is claimed is:

1. A compound represented by the formula (I), or a salt thereof:

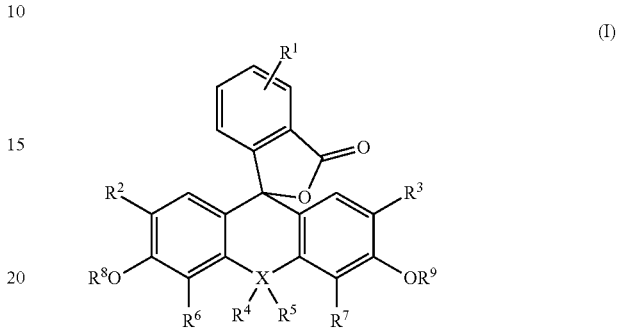

(I)

wherein, in the formula,
R¹ represents a hydrogen atom, or the same or different 1 to 4 monovalent substituents existing on the benzene ring;
R² and R³ independently represent a hydrogen atom, an alkyl group having 1 to 6 carbon atoms, a halogen atom, or a monovalent hydrophilic substituent;
R⁴ and R⁵ independently represent an alkyl group having 1 to 6 carbon atoms, or an aryl group having 1 to 6 carbon atoms;
R⁶ and R⁷ independently represent hydrogen atom, an alkyl group 1 to 6 carbon atoms, a halogen atom, or a monovalent hydrophilic substituent;
R⁸ and R⁹, which are the same or different, independently represent hydrogen atom or a monovalent group that is cleaved by contact with an object substance for measurement, provided that R⁸ and R⁹ are not simultaneously hydrogen atoms;
and X represents a silicon atom, a germanium atom, or a tin atom.

2. The compound or a salt thereof according to claim 1, wherein
R¹ represents a hydrogen atom or 1 to 3 monovalent substituents existing on the benzene ring wherein the substituents are selected from the group consisting of an alkyl group having 1 to 6 carbon atoms, an alkenyl group having 1 to 6 carbon atoms, an alkynyl group having 1 to 6 carbon atoms, an alkoxy group having 1 to 6 carbon atoms, hydroxy group, carboxy group, sulfonyl group, an alkoxycarbonyl group, a halogen atom, and amino group,
R² and R³ independently represent a hydrogen atom, an alkyl group having 1 to 6 carbon atoms, a halogen atom, or a monovalent hydrophilic substituent having an amino group substituted with one or two carboxyalkyl groups, which may form esters, as a partial structure;
R⁴ and R⁵ independently represent an alkyl group having 1 to 6 carbon atoms,
R⁶ and R⁷ independently represent a hydrogen atom or a halogen atom,
R⁸ and R⁹ represent a hydrogen atom or a monovalent group that is cleaved by contact with the same object substance for measurement, provided that R⁸ and R⁹ are not simultaneously hydrogen atoms; and
X represents a silicon atom.

3. The compound or a salt thereof according to claim 1, wherein
- $R^1$ represents a hydrogen atom or 1 to 3 monovalent substituents existing on the benzene ring wherein the substituents are selected from the group consisting of an alkyl group having 1 to 6 carbon atoms, an alkoxy group having 1 to 6 carbon atoms, hydroxy group, carboxy group, a halogen atom, and amino group,
- $R^2$ and $R^3$ independently represent a hydrogen atom or a monovalent hydrophilic substituent having one or two amino groups substituted with two carboxymethyl groups, which may form esters, as partial structures,
- $R^4$ and $R^5$ independently represent an alkyl group having 1 to 3 carbon atoms,
- $R^6$ and $R^7$ are both hydrogen atoms, chlorine atoms, or fluorine atoms,
- $R^8$ and $R^9$ represent a hydrogen atom or a monovalent group that is cleaved by the same reductase, oxidase, or hydrolase, provided that $R^8$ and $R^9$ are not simultaneously hydrogen atoms; and
- X represents silicon atom.

4. The compound or a salt thereof according to claim 1, wherein
- $R^1$ represents a hydrogen atom,
- $R^2$ and $R^3$ independently represent a hydrogen atom or an alkyl group having one or two amino groups substituted with two carboxymethyl groups, which may form acetoxymethyl esters, as partial structures, and wherein the alkyl group may have an oxo group, or contain an amide bond,
- $R^4$ and $R^5$ independently represent an alkyl group having 1 to 3 carbon atoms,
- $R^6$ and $R^7$ are both hydrogen atoms or chlorine atoms, and
- $R^8$ and $R^9$ represent a monovalent group that is cleaved by an enzyme selected from the group consisting of β-lactamase, cytochrome P450 oxidase, β-galactosidase, β-glucosidase, β-glucuronidase, β-hexosaminidase, lactase, alkaline phosphatase, matrix metalloprotease, and glutamyl transferase.

5. A method for measuring an object substance for measurement, which comprises
- contacting a compound represented by the formula (I) or salt thereof of claim 1 with the object substance for measurement, and then
- measuring fluorescence.

* * * * *

UNITED STATES PATENT AND TRADEMARK OFFICE
CERTIFICATE OF CORRECTION

| | | |
|---|---|---|
| PATENT NO. | : 9,250,232 B2 | Page 1 of 1 |
| APPLICATION NO. | : 14/378022 | |
| DATED | : February 2, 2016 | |
| INVENTOR(S) | : T. Nagano et al. | |

It is certified that error appears in the above-identified patent and that said Letters Patent is hereby corrected as shown below:

Claims

Column 34, line 34 (claim 1, line 13) please change "group 1" to -- group having 1 --

Signed and Sealed this
Twenty-eighth Day of June, 2016

Michelle K. Lee
*Director of the United States Patent and Trademark Office*